United States Patent [19]

Driver et al.

[11] Patent Number: 5,204,330
[45] Date of Patent: Apr. 20, 1993

[54] ANTIFUNGAL COMPOUNDS

[75] Inventors: Michael J. Driver, Slough; Alexander R. Greenlees; David T. MacPherson, both of Epsom, all of England

[73] Assignee: Beecham Group p.l.c., Brentford, England

[21] Appl. No.: 624,709

[22] Filed: Dec. 6, 1990

[30] Foreign Application Priority Data

Dec. 8, 1989 [GB] United Kingdom ............... 8927848
Jun. 18, 1990 [GB] United Kingdom ............... 9013574

[51] Int. Cl.$^5$ ...................... A61K 31/70; C07H 17/08
[52] U.S. Cl. ........................ 514/31; 536/6.5; 536/7.1; 536/115
[58] Field of Search .............. 536/6.5, 7.1, 115; 574/31

[56] References Cited

U.S. PATENT DOCUMENTS

| | | | |
|---|---|---|---|
| 4,035,568 | 7/1977 | Schaffner et al. | 536/115 |
| 4,468,511 | 8/1984 | Kirst et al. | 536/7.1 |
| 4,804,749 | 2/1989 | Fujiwara et al. | 536/7.1 |

FOREIGN PATENT DOCUMENTS 2173632  2/1971  France ................. 536/6.5

OTHER PUBLICATIONS

K. C. Nicolaou et al., Journal of the American Chemical Society vol. 110, 1988, pp. 4660-4672.

Primary Examiner—Johnnie R. Brown
Assistant Examiner—A. Varma
Attorney, Agent, or Firm—Hopgood, Calimafde, Kalil, Blaustein & Judlowe

[57] ABSTRACT

A compound of formula (I) or a pharmaceutically acceptable salt thereof:

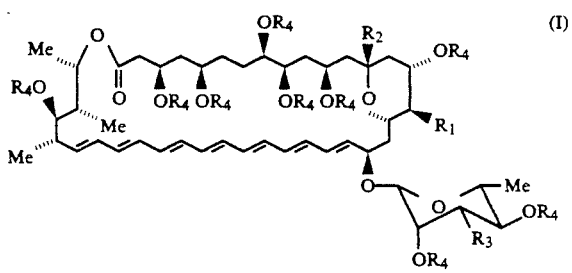

wherein: $R_1$ is a group $-CH_2-X$ where X is hydrogen, halogen, $-CN$, $-N_3$, $-OC(O)R_5$, $-S(O)_nR_5$, $-SH$, $-OC(O)NHR_5$, $-NHCONHR_5$ or $-NR_6R_7$, where $R_5$ is hydrogen optionally substituted $C_{1-8}$ alkyl, or aryl, heteroaryl, aryl $C_{1-4}$ alkyl or heteroaryl $C_{1-4}$ alkyl in each of which the aromatic moiety is optionally substituted with the proviso that when X is $-S(O)_nR_5$, $R_5$ does not represent hydrogen, $R_6$ and $R_7$ are independently hydrogen or $C_{1-6}$ alkyl, or one of $R_6$ and $R_7$ is hydrogen and the other is —formyl, $C_{2-8}$ alkanoyl, dialkoxyphosphoryl, aroyl, heteroaroyl, aryl $C_{1-4}$ alkanoyl, heteroaryl $C_{1-4}$ alkanoyl, $C_{1-8}$ alkylsulphonyl, arylsulphonyl, heteroarylsulphonyl, aryl $C_{1-4}$ alkylsulphonyl or heteroaryl $C_{1-4}$ alkylsulphonyl, where any aromatic moiety in $R_6$ or $R_7$ is optionally substituted, and n is 0, 1 or 2; $R_2$ is hydroxy or optionally substituted $C_{1-8}$ alkoxy; $R_3$ is an amino group or a derivative thereof; and each $R_4$ is hydrogen.

7 Claims, No Drawings

ANTIFUNGAL COMPOUNDS

The present invention relates to novel compounds having pharmacological activity, their preparation and their use in the treatment of fungal infections in animals, including humans.

The polyene macrolide amphotericin B, produced by *Streptomyces nodosus*, is widely used for the treatment of fungal infections.

Amphotericin B is the only complex polyene macrolide whose molecular structure and absolute configuration have been firmly established by x-ray crystallographic analysis Amphotericin B has the formula (A):

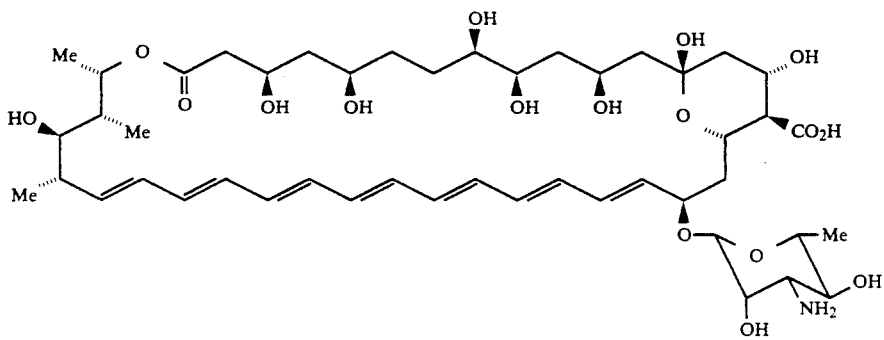

Novel derivatives of amphotericin B have now been prepared in which the 16-position carboxyl group is replaced by a methyl or derivatised methyl group. These compounds have been shown to have antifungal activity and have potential utility as antifungal agents.

Accordingly, the present invention provides a compound of formula (I) or a pharmaceutically acceptable salt thereof:

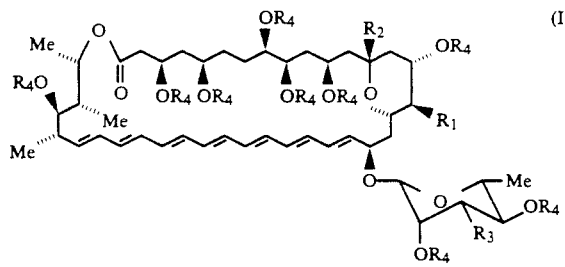

wherein: $R_1$ is a group $-CH_2-X$ where X is hydrogen, halogen, $-CN$, $-N_3$, $-OC(O)R_5$, $-S(O)_nR_5$, $-SH$, $-OC(O)NHR_5$, $-NHCONHR_5$ or $-NR_6R_7$, where $R_5$ is hydrogen optionally substituted $C_{1-8}$ alkyl, or aryl, heteroaryl, aryl $C_{1-4}$ alkyl or heteroaryl $C_{1-4}$ alkyl in each of which the aromatic moiety is optionally substituted with the proviso that when X is $-S(O)_nR_5$, $R_5$ does not represent hydrogen, $R_6$ and $R_7$ are independently hydrogen or $C_{1-6}$ alkyl, or one of $R_6$ and $R_7$ is hydrogen and the other is formyl, $C_{2-8}$ alkanoyl, dialkoxyphosphoryl, aroyl, heteroaroyl, aryl $C_{1-4}$ alkanoyl, heteroaryl $C_{1-4}$ alkanoyl, $C_{1-8}$ alkylsulphonyl, arylsulphonyl, heteroarylsulphonyl, aryl $C_{1-4}$ alkylsulphonyl or heteroaryl $C_{1-4}$ alkylsulphonyl, where any aromatic moiety in $R_6$ or $R_7$ is optionally substituted, and n is 0, 1 or 2; $R_2$ is hydroxy or optionally substituted $C_{1-8}$ alkoxy; $R_3$ is an amino group or a derivative thereof; and each $R_4$ is hydrogen.

It should be appreciated that when X is $NH_2$ and $R_2$ is hydroxy it may be advantageous to form a pharmacetically acceptable salt of the compound of formula (I) in order to enhance stability.

Unless otherwise specified the alkyl moiety of an alkyl or alkoxy group is preferably a $C_{1-6}$ alkyl group, more preferably a $C_{1-4}$ alkyl group and may be straight-chain or branched.

The term halogen includes fluorine, chlorine, bromine and iodine.

When used herein, the term aryl includes carbocyclic moieties, for example phenyl and naphthyl, preferably phenyl.

The term heteroaryl includes 5- or 6- membered monocyclic and 9- or 10- membered bicyclic heteroaryl.

In addition, 5- or 6- membered monocyclic and 9- or 10-membered bicyclic heteroaryl preferably contain one or two heteroatoms selected from nitrogen, oxygen and sulphur which in the case of there being more than one heteroatom may be the same or different. When 9- or 10- membered bicyclic heteroaryl, the two rings are fused, preferably with one 5-or 6- membered ring containing a single heteroatom.

An $R_5$ $C_{1-8}$ alkyl group and an $R_5$, $R_6$ or $R_7$ aryl or heteroaryl moiety may be mono-, di , or tri-substituted by groups including carboxy, nitro, alkoxycarbonyl, OH, $C_{1-6}$ alkyl, $C_{1-6}$ alkoxy, halogen, and $NR_6R_7$ where $R_6$ and $R_7$ are as defined in relation to formula (I).

When used herein, the term amino group derivative includes acyl derivatives, in particular acyl derivatives bearing a basic substituent such as N-D-lysyl and N-D-ornithyl derivatives, guanidine derivatives, and N-glycosyl derivatives. The preparation of suitable amino group derivatives is described in European Patent Publication 0 010 297 (Schering), European Patent Publication 0 031 722 (Dumex) and U.S. Pat. No. 4,195,172.

The term pharmaceutically acceptable salt encompasses solvates and hydrates. Thus where compounds of formula (I) or pharmaceutically acceptable salts thereof form solvates or hydrates, these also form an aspect of the invention.

Compounds of formula (I) can form acid addition salts with acids, such as conventional pharmaceutically acceptable acids, for example hydrochloric, hydrobromic, phosphoric, acetic, fumaric, salicylic, citric, lactic, mandelic, tartaric, oxalic, methanesulphonic, aspartic and ascorbic. The invention also extends to quaternary salts.

Values for X include hydrogen, iodo, $-CN$, $-N_3$, $-OC(O)R_5$ where $R_5$ is methyl, $-S(O)_nR_5$ where $R_5$ is phenyl and n is 0 or 2, and $-NR_6R_7$ where $R_6$ and $R_7$ are hydrogen or one of $R_6$ and $R_7$ is hydrogen and the other is acetyl, p-toluenesulphonyl or -P(O)(OEt)$_2$.

Values for $R_2$ include hydroxy and methoxy.

Suitably, $R_3$ is an amino group.

The present invention also provides a process for the preparation of compounds of formula (I) which process comprises the reaction of a compound of formula (II):

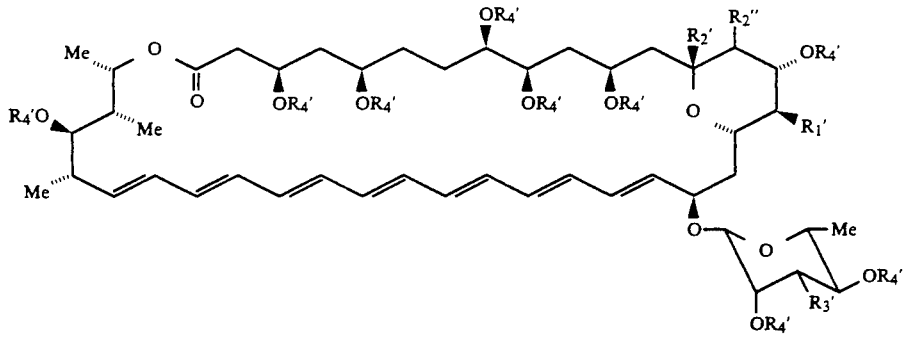

wherein: $R_1'$ is a group —$CH_2$—L where L is a leaving group (or a precursor to X); $R_2'$ is optionally substituted $C_{1-8}$ alkoxy and $R_2''$ is hydrogen, or $R_2'$ and $R_2''$ together are a bond; $R_3'$ is a protected amino group; and each $R_4'$ is hydrogen or a silyl protecting group; with a reagent providing a group X' where X' is X as defined for formula (I) or a group convertible thereto; and thereafter, optionally or as necessary and in any appropriate order converting X' to X, converting $R_2'$ to $R_2$ when $R_2''$ is hydrogen, or converting $R_2'$ to $R_2$ and $R_2''$ to hydrogen when $R_2'$ and $R_2''$ together are a bond, converting $R_3'$ to an $R_3$ amino group, forming an amino group derivative, removing any $R_4'$ silyl protecting groups, interconverting $R_1$, interconverting $R_2$, and forming a pharmaceutically acceptable salt.

Suitable values for L when a leaving group include derivatised hydroxy such as mesyloxy, tosyloxy, trifluoromethanesulphonyloxy and phosphorus derivatives such as tri-n-butylphosphoniumoxy [—$OP^+$(n-Bu)$_3$], and halogen.

An L hydroxy group may also serve as a precursor to X, for example when X is —$OC(O)R_5$ or —$OC(O)H$. In this case the reagent providing X' is an suitably an acyl cation, $R_5CO^+$ derived from, for example, a carboxylic acid anhydride.

When L is a leaving group it will be appreciated that the group X' will generally be presented for reaction with a compound of formula (II) in the form of a reagent where X' is an anion in combination with a suitable counter ion. Thus when X is —$N_3$, such that X' is $N_3^-$, the counter ion may, for example, be a sodium or a tetramethylguanidinium cation.

When X' is $N_3^-$ derived from sodium azide, L is suitably mesyloxy and the reaction may be carried out under anhydrous conditions in refluxing benzene in the presence of a phase transfer catalyst such as tetra-n-butylammonium bromide. When X' is $N_3$— derived from tetramethylguanidinium azide, an L hydroxyl group may be converted in situ to a trifluromethanesulphonyloxy leaving group which is displaced by azide ion. The reaction is carried out at reduced temperatures under anhydrous conditions in an inert solvent such as dichloromethane.

When X is halogen, for example iodo, a compound of formula (II) in which L is a leaving group may be reacted with a tetraalkylammonium halide, for example tetra-n-butylammonium iodide.

When X is SH, a compound of formula (II) in which L is a leaving group may be reacted with $H_2S$ in the presence of a suitable base.

Similarly, when X is —$S(O)_nR_5$ a compound of formula (II) may be reacted with a compound, $HS(O)_nR_5$ where n is 0 or 2 or a suitable salt thereof. Where n is 0, the resulting sulphide may be oxidised to the corresponding sulphoxide (n=1) or sulphone (n=2).

When X is —$NHCONHR_5$, a compound of formula (II) in which L is $NH_2$ may be reacted with an isocyanate $R_5NCO$ or a compound $ClC(O)NHR_5$ in the presence of a suitable base.

When X is —$OC(O)NHR_5$, a compound of formula (II) in which L is OH may be reacted with an isocyanate $R_5NCO$ or a compound $ClC(O)NHR_5$ in the presence of a suitable base. In the above-identified reactions, it is preferable for the secondary hydroxyl groups on the amphotericin B nucleus to be in protected form. Thus $R_4'$ in the compound of formula (II) is a silyl protecting group.

It is possible to prepare certain compounds of formula (I) from compounds of formula (II) in which the secondary hydroxy groups are unprotected (i.e. each $R_4'$ is hydrogen) when X' is derived from a reagent which may be selective for L, particularly where L is a hydroxyl group or derivative thereof. For example, when X is —$S(O)_nR_5$ wherein n is 0 and $R_5$ is phenyl, an 'unprotected' ($R_4'$=H) compound of formula (II) in which L is hydroxy may be reacted with diphenyl disulphide in the presence of tri-n-butylphosphine at reduced temperature in an inert solvent such as tetrahydrofuran.

When X' is other than X, for example when X' is azido ($N_3$) and X is amino ($NH_2$), conversion of X' to X may be effected either before or after removal of the $R_4'$ silyl protecting groups and conversion of $R_3'$ to an $R_3$ amino group by removal of the amine protection group. Conversion of X' azido ($N_3$) to X amino ($NH_2$) may be carried out by treatment of the azide with a phosphine derivative, for example triphenylphosphine or a trialkylphosphine such as triethylphosphine in the presence of water.

Alternatively, the conversion may be carried out under anhydrous conditions using propane-1,3-dithiol in the presence of triethylamine. A suitable organic solvent for the reaction under aqueous conditons is tetrahydrofuran whilst the anhydrous reaction is suitably carried out in an alcoholic solvent such as methanol.

Conversion of X' azido ($N_3$) to an X is $NHP(O)(OEt)_2$ radical may be carried out by treatment with the appropriate phosphite derivative. For example, a compound in which X is $NHP(O)(OEt)_2$ may be prepared by reaction with triethylphosphite, preferably when $R_4'$ is a silyl protecting group.

Conversion of X' halogen, for example iodo, to X hydrogen may be carried out by reduction, suitably using a borohydride reagent such as lithium triethylborohydride.

Interconversion of $R_1$ may be carried out using standard chemical transformations. For example, a compound in which $R_1$ is $CH_2NH_2$ (X=$NH_2$) may be chemically modified by acylation or by reaction with sulphonyl derivatives.

The process according to the invention may be carried out using a compound of formula (II) in which $R_2'$ is $C_{1-8}$ alkoxy, preferably methoxy, and $R_2''$ is hydrogen, or using a compound of formula (II) in which $R_2'$ and $R_2''$ together are a bond, or mixtures thereof.

Suitable values for amine protection groups in $R_3'$ include 9-fluorenylmethoxycarbonyl, allyloxycarbonyl, 2,2,2-trichloroethoxycarbonyl, 2-phenylsulphonylethoxycarbonyl and 2-trimethylsilylethoxycarbonyl. Preferred amine protection groups are 9-fluorenylmethoxycarbonyl and allyloxycarbonyl.

Suitable $R_4'$ silyl protecting groups include trimethylsilyl, triethylsilyl and t-butyldimethylsilyl. Preferably $R_4'$ is triethylsilyl.

In compounds of formula (II) where $R_2'$ is $C_{1-8}$ alkoxy and $R_2''$ is hydrogen, $R_2'$ may be converted to an $R_2$ hydroxy group under acid-catalysed conditions after removal of the $R_4'$ silyl protecting groups, using water or a mixture of water and tetrahydrofuran as solvent, preferably using a solvent mixture comprising up to 50% water in tetrahydrofuran.

Similarly, compounds of formula (II) where $R_2'$ and $R_2''$ together are a bond may be hydrated under acid-catalysed conditions to give compounds of formula (I) in which $R_2$ is hydroxy.

A suitable acid catalyst for these reactions is 10-camphorsulphonic acid or pyridinium p-toluene-sulphonate.

Compounds of formula (II) in which $R_2'$ and $R_2''$ together form a bond may be converted directly to compounds of formula (I) in which $R_2$ is $C_{1-8}$ alkoxy by the acid-catalysed addition of the appropriate $C_{1-8}$ alkyl alcohol, or alternatively, indirectly via initial hydration of the double bond followed by exchange of the $R_2$ hydroxyl group so formed, using the appropriate $C_{1-8}$ alkyl alcohol. These conversions are suitably carried out in the presence of 10-camphorsulphonic acid or pyridinium p-toluenesulphonate.

Conversion of certain protected amino groups $R_3'$ to $R_3$ amino may be carried out under basic conditions. For example, an amine protection group, such as 9-fluorenylmethoxycarbonyl, may be removed under basic conditions in a solvent such as methanolic dimethyl sulphoxide. Suitable bases for amine deprotection include ammonia, dialkylamines such as dimethylamine and diethylamine, trialkylamines such as triethylamine, cyclic amines and especially cyclic secondary amines such as morpholine, piperazine and more especially piperidine, and diazabicyclic bases such as 1,5-diazabicyclo[4.3.0]non- 5-ene (DBN) and preferably 1,8-diazabicyclo[5.4.0]undec-7-ene (DBU).

The amine deprotection may be carried out using from 1-10 equivalents of base, preferably from 1-2 equivalents, at reduced or elevated temperatures, for example from $-30°$ C. to 50° C. and preferably from 0° C. to room temperature, over a time period ranging from 1 minute to 5 hours and preferably from 30 minutes to 2.5 hours.

An allyloxycarbonyl amine protection group is stable to amine bases and is therefore particularly suitable for the preparation of compounds in which $R_1$ has basic properties. An allyloxycarbonyl group may be removed via palladium catalysis, suitable in the presence of $PdCl_2(PPh_3)_2$ and treatment with tri n-butyl tin hydride.

$R_4'$ silyl protecting groups may be removed using known deprotection methods, for example using a solution of hydrogen fluoride-pyridine in tetrahydrofuran, at normal or reduced temperature, for example from $-10°$ C. to 50° C. and preferably from 0° C. to room temperature, over a time period up to 60 hours and preferably from 4 to 24 hours.

Intermediate compounds of formula (II) may be prepared from the natural product amphotericin B by carrying out the following steps in any appropriate order:
(a) converting the 16-position carboxy group to an activated form followed by reduction and further derivatisation, as necessary, to give $R_1'$.
(b) selectively exchanging the 13-position anomeric hydroxyl group to give an $R_2'$ $C_{1-8}$ alkoxy group or preparing a compound in which $R_2'$ and $R_2''$ together are a bond;
(c) protecting the amine function of the 19-position sugar moiety to form an $R_3'$ protected amino group.
(d) converting free hydroxyl groups, as necessary, to $-OR_4'$ where $R_4'$ is a silyl protecting group.

It will be understood that the term activated carboxylic acid derivative when used herein in relation to (a) includes a carboxylic acid group modified by chemical reaction into an activated form amenable to the chosen transformations which provide $R_1'$.

The term activated carboxylic acid derivative includes alkyl, aryl and heteroaryl esters and thioesters, acid halides, acid anhydrides, and amides such as N-methyl-N-methoxycarbonyl and imidazoylcarbonyl.

A carboxylic acid derivative activated for reaction with a reducing agent to provide $R_1'$ where L is hydroxy is suitably a thioester and preferably a heteroarylthioester such as a pyridylthioester. Favourably $R_1'$ is a 2-pyridylthioester.

A suitable reducing agent for this reduction is lithium borohydride. The reaction may be carried out in an inert solvent such as diethyl ether or tetrahydrofuran, preferably diethyl ether.

The 16-position carboxyl group may be converted to an $R_1'$ 2-pyridylthioester using 2-thiopyridyl chloroformate in an inert solvent such as tetrahydrofuran, diethyl ether or dichloromethane, preferably diethyl ether, at temperatures ranging from reduced to elevated, such as from $-20°$ C. to 50° C., preferably 0° C. to room temperature.

Conversion of $R_1'$ in which L is hydroxy to other values of L such as derivatised hydroxy or halogen may be carried out using procedures described herein.

The 13-position anomeric hydroxyl group may be selectively exchanged using the appropriate $C_{1-8}$ alkyl alcohol in the presence of an acid catalyst such as 10-camphorsulphonic acid or pyridinium p-toluene-sulphonate under anhydrous conditions. The reaction may be carried out in an inert solvent such as tetrahydrofuran and the alcohol may act either wholly or partially as the solvent. The reaction is conveniently carried out in the presence of an $H_2O$-scavenger such as molecular sieves and under an inert atmosphere.

Amine protection groups may be introduced by standard procedures. For example, a 9-fluorenylmethoxycarbonyl amine protection group may be introduced by addition of 9-fluorenylmethylchloroformate to a solution of the primary amine in methanol-dimethylformamide under anhydrous conditions, in the presence of a base such as potassium carbonate.

Alternatively a 9-fluorenylmethoxycarbonyl group may be introduced by addition of N-(9-fluorenylmethoxycarbonyloxy)succinimide to a slurry of the primary amine in methanol-dimethylformamide under anhydrous conditions in the presence of a base such as pyridine. An allyloxycarbonyl group may similarly be introduced by addition of allyl succinimidyl carbonate.

Free secondary hydroxyl groups may be silylated using standard procedures. The reaction with silyating agents such as trimethylsilyl trifluoromethane-sulphonate and triethylsilyl trifluoromethanesulphonate may be carried out in an inert solvent, for example dichloromethane, hexane or diethyl ether, under an inert atmosphere at reduced temperatures, for example from 0° C. to 5° C. The reaction is conveniently effected using an excess of the silylating agent in the presence of a weak base, for example a pyridine derivative such as 2,6-lutidine. Alternatively, when a liquid, the base may replace the solvent. The reaction time is dependent on the size of the silyl group, ranging from a few minutes for a trimethylsilyl group to several hours for larger silyl groups.

The introduction of $R_4'$ silyl protecting groups is accompanied by elimination or partial elimination of the 13-position substituent such that in compounds of formula (II) variables $R_2'$ and $R_2''$ may be $C_{1-8}$ alkoxy and hydrogen respectively or $R_2'$ and $R_2''$ may together be a bond. The extent of the elimination varies according to the solvent; it is significant when the solvent is dichloromethane, but negligible when the solvent is hexane or diethyl ether.

Where the silylation reaction results in a mixture of compounds, these may be separated by chromatographic techniques. Alternatively the preparation of compounds of formula (I) may proceed using a mixture of compounds of formula (II).

If required, a compound of formula (I) in which $R_2$ is hydroxy may be converted to a compound of formula (I) in which $R_2$ is $C_{1-8}$ alkoxy using step (b) hereinbefore described for the preparation of intermediate compounds of formula (II).

The compounds of the formula (I) and their pharmaceutically acceptable salts are anti-fungal agents, potentially useful in combating fungal infections in animals, including humans. For example they are potentially useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus*, Coccidioides, Paracoccidioides, Histoplasma or Blastomyces spp. They may also be of use in treating eumycotic mycetoma, chromoblastomycosis, and phycomycosis.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

The invention also provides a process for preparing a pharmaceutical composition which comprises admixing a compound of formula (I) or a pharmaceutically acceptable diluent or carrier.

For human use, the antifungal compounds of the formula (I) or pharmaceutically acceptable salts thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, it is expected that the daily dosage level of the antifungal compounds of the formula (I) will be from 0.1 to 1 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Within the indicated dose range, no adverse toxicological effects have been observed with the compounds of the invention which would preclude their administration to suitable patients for the treatment of fungal infections.

The present invention further provides a compound of formula (I) or a pharmaceutically acceptable salt thereof for use as an active therapeutic substance.

A compound for use as an active therapeutic substance is intended for use in the treatment of disorders in animals including humans. As stated above, compounds of formula (I) and their pharmaceutically acceptable salts have anti-fungal activity and are potentially useful in combating fungal infections in animals including humans.

Accordingly the present invention further provides a compound of formula (I) or a pharmaceutically acceptable salt thereof for use in the treatment of fungal infections.

The present invention additionally provides a method of treatment of fungal infections in animals, including humans, which comprises administering an effective anti-fungal amount of a compound of formula (I) or a pharmaceutically acceptable salt thereof to the animal.

The present invention also provides the use of a compound of formula (I) or a pharmaceutically acceptable salt thereof for the manufacture of a medicament for use in the treatment of fungal infections in animals, including humans.

The following Examples illustrate the preparation of novel compounds of the invention and the following Descriptions illustrate the preparation of intermediates thereto.

The abbreviations 'TES', 'Fmoc' and 'alloc' are used to represent triethylsilyl, 9-fluoroenylmethoxycarbonyl and allyloxycarbonyl groups respectively.

DESCRIPTION 1

N-(9-Fluorenylmethoxycarbonyl)amphotericin B (D1)

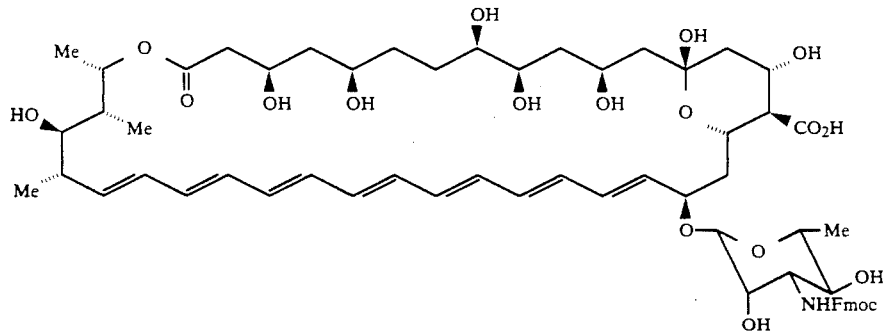

To a solution of amphotericin B (0.50 g, 0.54 mmol) and anhydrous potassium carbonate (0.17 g, 1.2 mmol) in dry dimethylsulphoxide (10 ml) and dry methanol (2 ml) under a nitrogen atmosphere at 0° C., was added solid 9-fluorenylmethyl chloroformate (0.21 g, 0.81 mmol). After stirring for 1 hour a further portion of 9-fluorenylmethyl chloroformate (0.04 g, 0.17 mmol) was added. After 0.25 hours the reaction mixture was poured into distilled water (200 ml). The precipitate was collected by centrifugation, dissolved in methanol and evaporated in vacuo. The residue was dissolved in the minimum volume of a mixture of tetrahydrofuran and methanol (1:1) and poured into distilled water (200 ml, adjusted to pH 3.2 by the addition of glacial acetic acid). The preciptate was centrifuged, washed with water and dried in vacuo to give the title compound (D1) which was used without further purification.

DESCRIPTION 2

N-(9-Fluorenylmethoxycarbonyl)-13-O-methylamphotericin B (D2)

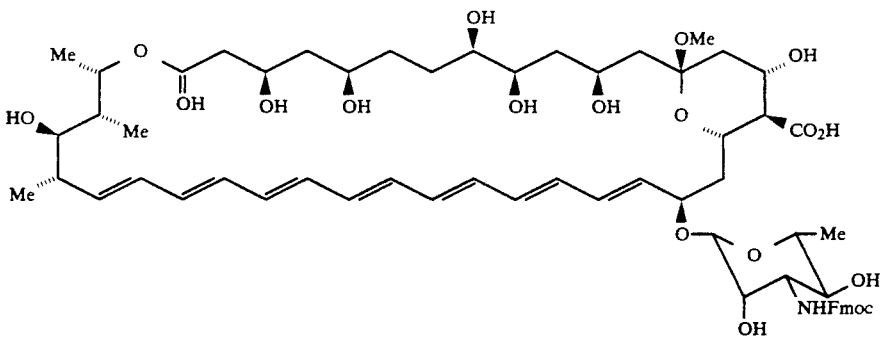

Method A

N-(9-Fluorenylmethoxycarbonyl)amphotericin B (D1) (1.85 g, 1.61 mmol) and d-10-camphorsulphonic acid (156 mg, 0.67 mmol) were stirred in dry tetrahydrofuran (10 ml)/methanol (60 ml) at room temperature under nitrogen. After 15 minutes, triethylamine (0.14 ml, 102 mg, 1.01 mmol) was added, the mixture was filtered, concentrated to ca. 10 ml and poured into diethylether/n-hexane (800 ml 1:1). The precipitated product was collected by centrifugation, washed with diethylether/ethylacetate (1:1) and dried to give the title compound (D2) as a yellow powder.

Method B

N-(9-Fluorenylmethoxycarbonyl)amphotericin B (4.99 g, 4.35 mmol) and pyridinium p-toluenesulphonate (5.04 g, 20.1 mmol) were stirred in methanol (450 ml)/tetrahydrofuran (150 ml) at room temperature for 1.5 hours. Triethylamine (2.65 g, 3.65 ml, 26.2 mmol) was added, the mixture was concentrated to 30 ml and added to saturated sodium bicarbonate solution (2 L). The precipitated product was collected by filtration, washed with water and dried to give the title compound (D2) as a yellow powder.

HPLC: Reverse phase ODS 5μ 250×4.6 mm column; eluant 80% methanol-20% pH 3 phosphate buffer - 1 ml.min$^{-1}$; detection wavelength 350 nm; retention time: 7.6 minutes.

DESCRIPTION 3

N-(9-Fluorenylmethoxycarbonyl)-13-O-methyl-3,5,8,9,11,15,35,2',4'-nona-O-triethylsilylamphotericin B (D3)

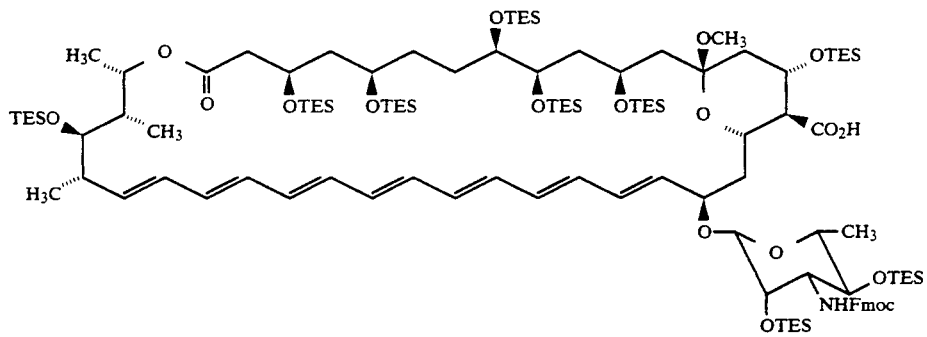

N-(9-Fluorenylmethoxycarbonyl)-13-O-methylamphotericinB (D2) (4.97 g, 4.3 mmol) was suspended in dry n-hexane (150 ml) at 0° C. under nitrogen and treated with 2,6-lutidine (8.3 g, 8.9 ml, 77 mmol) followed by triethylsilyl trifluoromethanesulphonate (15.8 g, 13.6 ml, 60 mmol). After stirring at 0° C. for 2hrs further batches of 2,6-lutidine (4.5 ml) and triethylsilyl trifluoromethanesulphonate (6.8 ml) were added in two portions 15 minutes apart. Stirring was continued for a further 1 hr and the mixture was filtered and concentrated in vacuo. Purification by chromatography on silica gel (eluting with ethyl acetate/n-hexane mixtures) gave the title compound (D3) as a yellow/orange foam.

DESCRIPTION 4

N-(9-Fluorenylmethoxycarbonyl)-13-O-methyl-3,5,8,9,11,15,35,2',4'-nona-O-triethylsilylamphotericin B (2-pyridylthio)ester (D4)

The product of Description 3 (823 mg, 0.38 mmol) was stirred at 0° C. in dry diethyl ether (15 ml) and treated with triethylamine (50 mg, 0.07 ml, 0.49 mmol) followed by 2-thiopyridyl chloroformate (105 mg, 3 ml of 35 mg/ml solution in dichloromethane). After stirring at 0° C. for 30 minutes, the mixture was diluted with diethyl ether (80 ml), dried over anhydrous magnesium sulphate, filtered and evaporated in vacuo. Purification by flash chromatography on silica gel eluting with 10% ethyl acetate in n-hexane gave the title compound (D4) as a yellow/orange foam.

Rf: 0.45 (silica), 15% ethyl acetate in n-hexane. δH 270MHz ((CD$_3$)$_2$CO) 8.73(1H, d, J 5Hz), 7.95(1H, dt, J 7.5, 2Hz), 7.88(2H, d, J 7.2Hz), 7.73(1H, d, J 7.5Hz), 7.71(2H, d, J7Hz), 7.50–7.25 (5H, m), 6.70–6.08(12H, series of m), 5.97(1H, dd, J 5.5, 15Hz), 5.50(1H, dd, J 9.6, 15Hz), 5.30(1H, d, J 9.6Hz), 4.78(1H, m), 4.65(1H, m), 4.62(1H, s), 4.56–4.42(2H, m), 4.38–3.96(6H, series of m), 3.92(1H, d, J 3Hz), 3.87(1H, dd, J 9, 3Hz), 3.77–3.55(3H, m), 3.50–3.35(2H, m), 3.13(3H, s), 2.77(1H, t, J 9Hz), 2.59(2H, d, J 6.4Hz), 2.44(1H, m), 2.32(1H, dd, J 6.4, 14Hz), 2.15–1.40(14H, series of m), 1.23(3H, s, J 5Hz), 1.18(3H, s, J 6Hz), 1.15–0.86(87H, m), 0.85–0.45(54H, series of m)ppm.

IR ν$_{max}$ (thin film) : 3459, 2965, 2920, 2888, 1737 (shoulder at 1710), 1578, 1510, 1460, 1418, 1382, 1312, 1241, 1115, 1080, 1010, 740cm$^{-1}$.

Mass spectrum : FAB(3-NOBA/Na matrix). Observed mass MNa$^+$ 2302, calculated for $C_{122}H_{214}N_2O_{18}Si_9SNa^+$, 2302.

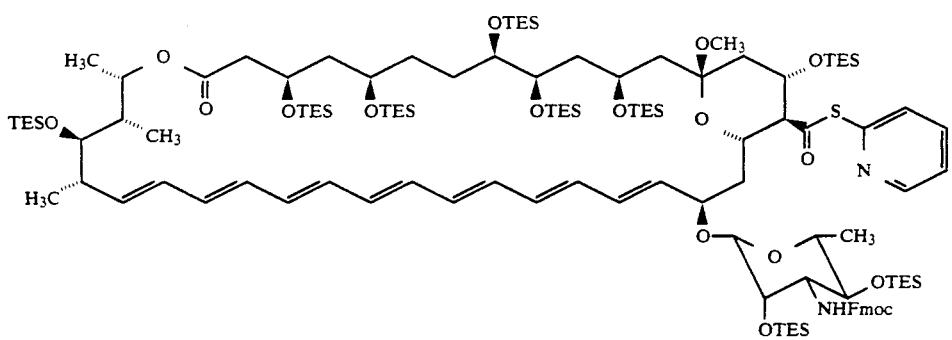

DESCRIPTION 5

N-(9-Fluorenylmethoxycarbonyl)-16-decarboxy-16-hydroxymethyl-13-O-methyl-3,5,8,9,11,15,35,2',4'-nona-O-triethylsilylamphotericin B (D5)

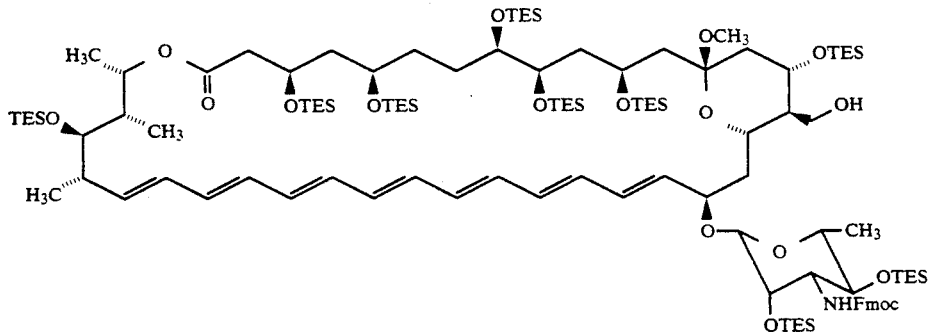

N-(9-Fluorenylmethoxycarbonyl)-13-O-methyl-3,5,8,9,-11,15,35,2',4'-nona-O-triethylsilylamphotericin B (2-pyridylthio)ester (D4) (3.26 g, 1.43 mmol) was stirred in diethyl ether (60 ml), under nitrogen at room temperature and treated with lithium borohydride (0.150 g, 6.89 mmol). After 2 hrs the mixture was cooled to 0° C., saturated ammonium chloride solution was added and the mixture was stirred vigorously for a few minutes. The product was extracted into diethyl ether and the combined organic extracts were dried over anhydrous magnesium sulphate, filtered and then concentrated in vacuo. Purification by flash chromatography on silica gel (eluting with diethyl ether/dichloromethane mixtures) gave the title compound as a yellow glassy solid.

Rf: 0.44 (silica), 2% diethylether indichloromethane.
δH 400 MHz ((CD$_3$)$_2$CO) 7.87(2H, d, J 7.5Hz), 7.69(2H, d, J 7.4Hz), 7.43(2H, t, J 7.4Hz), 7.34((2H, t, J 7.4Hz), 6.54–6.10(12H, series of m), 6.06(1H, dd, J 15.4 6.1Hz), 5.51(1H, dd, J 14.8, 9.7Hz), 5.37(1H, d, J 9.8Hz), 4.78(1H, s), 4.78–4.62(2H, m), 4.48(1H, dd, J 10.4, 6.5Hz), 4.34(1H, dd, J 10.4, 6.5Hz), 4.30–4.08(4H, m), 4.05–3.76(6H, m), 3.74–3.58(3H, m), 3.47(1H, t, J 9.0Hz), 3.35(1H, m), 3.12(3H, s), 2.63–2.50 (2H, m), 2.48–2.36(2H, m), 2.12(1H, dd, J 12.3, 4.4Hz), 2.07–1.25(14H, series of m), 1.25(3H, d, J 6.1Hz), 1.18(3H, d, J 6.0Hz), 1.14–0.85(87H, series of m), 0.80–0.53(54H, series of m)ppm. The OH proton was not observed.

IR $\nu_{max}$ (thin film): 3600–3300 (weak, broad), 3450, 2958, 2915, 2879, 1737, 1510, 1461, 1414, 1380, 1309, 1240, 1193, 1110, 1078, 1007, 905, 839, 740, 725, 674cm$^{-1}$.

Mass spectrum: FAB(3-NOBA/Na matrix) observed mass MNa$^+$ 2195, calculated for C$_{117}$H$_{213}$NO$_{18}$Si$_9$Na$^+$, 2195.

DESCRIPTION 6

N-(9-Fluorenylmethoxycarbonyl)amphotericin B methyl ester (D6)

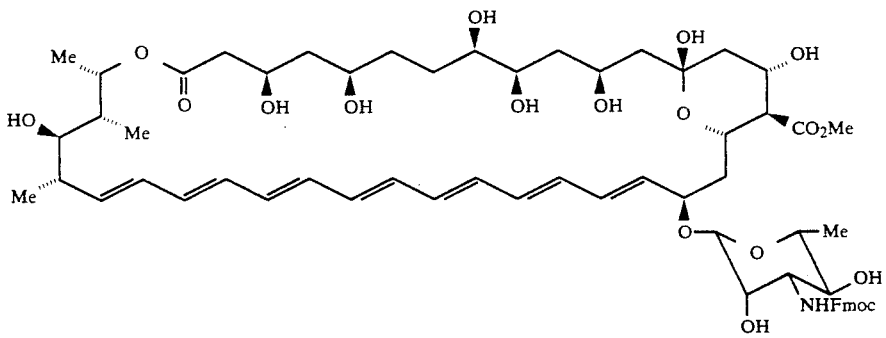

Crude N-(9-fluorenylmethoxycarbonyl)amphotericin B (D1) (2.11 g, 1.84 mmol) was dissolved in 1:1 dimethylsulphoxide and methanol (27 ml). At 0° C. and with stirring, a solution of diazomethane in diethyl ether (13 ml) was added over 0.3 hours. The diazomethane was generated from; Diazald ® (1.97 g, 9.20 mmol); potassium hydroxide (0.56 g, 10.00 mmol); water (1 ml) and 2-(2-ethoxyethoxy)ethanol (3.3 ml). The reaction was stirred for a further 0.5 hours and then quenched cautiously with glacial acetic acid. The product was precipitated by pouring into diethyl ether (4 liters), filtered, washed with diethyl ether and dried in vacuo giving the title compound (D6) as a yellow solid.

Hplc: Reverse phase using: ODS 5μ 250×4.6 mm column; eluant 80% methanol -20% pH3 phosphate buffer - 1 ml/min; detection wavelength 350 nm; retention time 18.8 minutes.

DESCRIPTION 7

N-(9-Fluorenylmethoxycarbonyl)-13-O-methylamphotericin B methyl ester (D7)

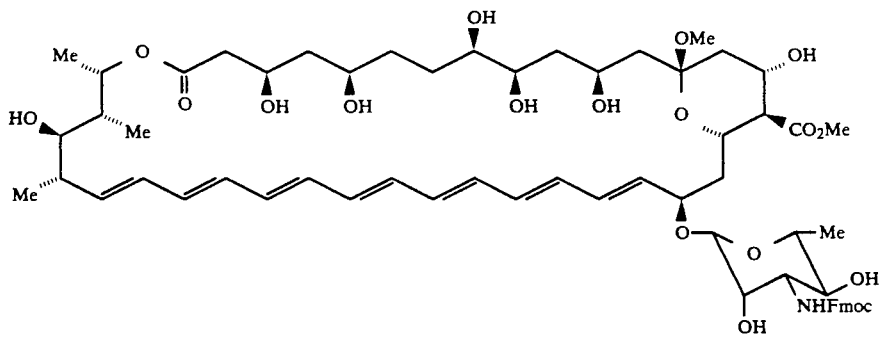

Method A
N-(9-Fluorenylmethoxycarbonyl)amphotericin B methyl ester (D6) (7.38 g, 6.36×10⁻³ mol) suspended in a 4:1 mixture of dry methanol/tetrahydrofuran (400 ml) was treated with 10-camphorsulphonic acid (1.42 g, 5.66×10⁻³ mol), to lower the pH of the reaction mixture to ca. 2.5. After 1.2 h the reaction mixture was neutralised with triethylamine (700 μl, 5.02×10⁻³ mol), concentrated and poured into diethyl ether (10 liters) The yellow product, N-(9-fluorenylmethoxycarbonyl)-13-O-methylamphotericin B methyl ester (D7), was filtered, washed with diethyl ether and dried under vacuum.

Method B
N-(9-Fluorenylmethoxycarbonyl)amphotericin B methyl ester (D6) (10.25 g, 8.94 mmol) suspended in a 3:1 mixture of dry methanol/tetrahydrofuran (1.06 L) was treated with pyridininium p-toluenesulphonate (12.42 g, 49.4 mmol). After 2.0 h the reaction mixture was treated with triethylamine (8.26 ml, 59.3 mmol), concentrated and poured into saturated sodium hydrogen carbonate solution (5 liters). The yellow product, N-(9-fluorenylmethoxycarbonyl)-13-O-methylamphotericin B methyl ester (D7), was filtered, washed with water and dried under vacuum.

Hplc: Reverse phase ODS 5μ 250×4.6 mm column; eluant 78% methanol-22% pH 3 phosphate buffer - 1 mlmin⁻¹; detection wavelength 350 nm; Retention time: 12.7 minutes. Mass spectrum FAB (thioglycerol matrix) observed mass 1196 -calculated mass for $C_{64}H_{87}NO_{19}Na$, 1196.6.

DESCRIPTION 8

N-(9-Fluorenylmethoxycarbonyl)-16-decarboxy-16-hydroxymethyl-13-O-methyl amphotericin B (D8)

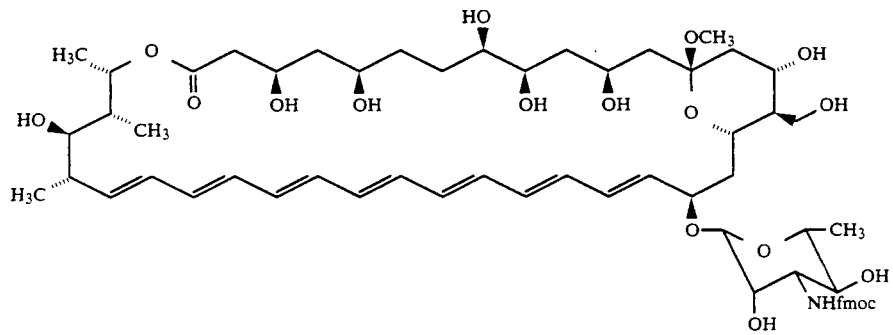

N-(9-Fluorenylmethoxycarbonyl)-13-O-methylamphotericin B methyl ester (D7) (6.75 g, 5.75×10⁻³ mol), dissolved in a 3:1 mixture of methanol/tetrahydrofuran (185 ml), was treated with sodium borohydride (5.65 g, 1.50×10⁻¹ mol) at 0° C. After addition of the sodium borohydride the reaction mixture was allowed to reach ambient temperature. After 30 minutes saturated sodium hydrogen carbonate solution (3 ml) was added to the reaction mixture. The mixture was concentrated and poured into saturated sodium hydrogen carbonate solution (8 liters). The yellow product, N-(9-fluorenylmethoxycarbonyl)-16-decarboxy-16-hydroxymethyl-13-O-methylamphotericin B was filtered, washed with water and dried under vacuum.

The crude material was purified by means of column chromatography on normal phase silica-gel eluting with dichloromethane and methanol mixtures to give the title compound (D8).

IR νmax (KBr disc) 3415, 3010, 2925, 1710, 1510, 1445, 1375, 1320, 1180, 1065, 1005, 900, 845, 760 and 740 cm⁻¹.

DESCRIPTION 9

N-(9-Fluorenylmethoxycarbonyl)-16-decarboxy-16-methanesulphonyloxymethyl-13-O-methyl-3,5,8,9,11,15,35,2',4'-nona-O-triethylsilylamphotericin B (D9)

DESCRIPTION 10

N-(9-Fluorenylmethoxycarbonyl)-16-azidomethyl-16-decarboxy-13-O-methyl-3,5,8,9,11,15,35,2',4'-nona-O-triethylsilylamphotericin B (D10)

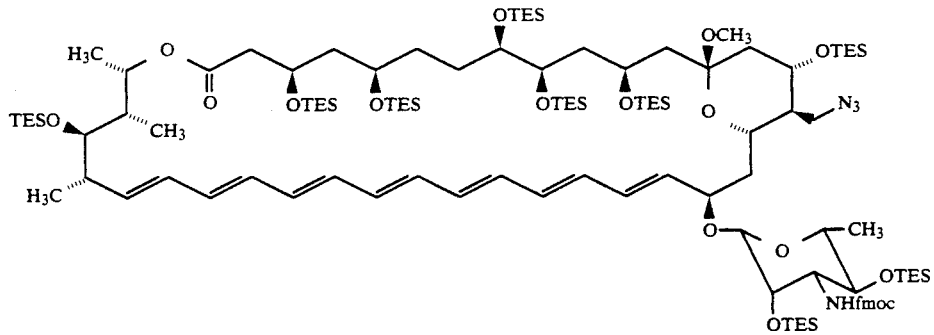

Method A

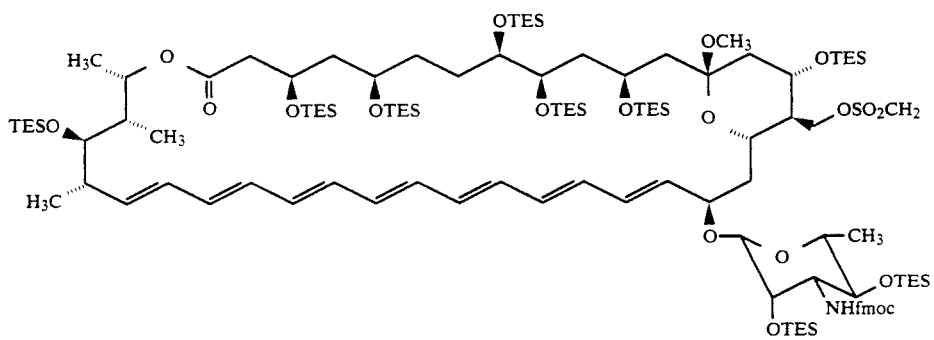

The alcohol of Description 5 (0.760 g, 0.35 mmol) was cooled to 0° C. under nitrogen in dry dichloromethane (10 ml) and treated with triethylamine (0.106 g, 0.146 ml, 1.05 mmol) followed by methanesulphonyl chloride (0.080 g, 0.054 ml, 0.70 mmol). After stirring for 30 minutes the same quantities of triethylamine and methanesulphonyl chloride were added again and stirring was continued for a further 20 minutes at 0° C. The mixture was diluted with diethyl ether, washed with water, dried over anhydrous magnesium sulphate, filtered and concentrated in vacuo. Purification by flash chromatography on silica gel (eluting with diethyl ether/dichloromethane mixtures) gave the title compound (D9).

IR νmax (thin film):3465,2970,2925,2895,1745,1520,1473, 1427,1390,1375,1263,1192,1120,1090,1019,985,918,846, 752,685 cm$^{-1}$.

δH 270MHz ((CD$_3$)$_2$CO): 7.88 (2H,d,J 7.4Hz), 7.70 (2H,d,J 7.4Hz), 7.43 (2H,t,J 7.2Hz), 7.34 (2H,t,J 7.4Hz), 6.55–6.00 (13H,series of m), 5.43 (1H,dd,J 15.1, 9.7Hz) 5.34 (1H,d,J 9.9Hz), 4.82–4.63 (3H,m, including s at 4.75), 4.57–3.55 (15H, series of m), 3.47 (1H,t,J 9.1Hz), 3.42 (1H,m), 3.15 (6H,s), 2.67–2.35 (3H,m), 2.32–2.10 (2H,m), 2.10–1.40 (14H, series of m), 1.24 (3H,d,J 6.1Hz), 1.18 (3H,d,J 6.1Hz), 1.12–0.84 (87H, series of m), 0.79–0.50 (54H, series of m) ppm.

Mass spectrum: FAB (3-NOBA/sodium matrix) Observed mass 2273, calculated mass for $C_{118}H_{215}NO_{20}Si_9SNa^+$, 2273.

A mixture of the mesylate of Description 9 (0.319 g, 0.142 mmol), sodium azide (0.037 g, 0.567 mmol) and tetra n-butylammonium bromide (0.005 g, 0.0142 mmol) was refluxed in dry benzene (4 ml) under nitrogen for 24 hours. After cooling the mixture was filtered, diluted with diethyl ether, washed with water (2x), dried over anhydrous magnesium sulphate, filtered and concentrated in vacuo. Purification by column chromatography on silica gel (eluting with n-hexane/ethyl acetate and n-hexane/diethyl ether mixtures) gave the title compound (D10).

Method B

A solution of the alcohol of Description 5 (2.93 g, 1.35 mmol) and pyridine (0.47 g, 0.48 ml, 5.92 mmol) in dry dichloromethane (60 ml) was cooled to −10° C. under nitrogen. To this mixture was added a solution of trifluoromethanesulphonic anhydride (0.84 g, 0.50 ml, 2.96 mmol) in dichloromethane (10 ml) via a canula. After stirring for 5 minutes at −10° C., tetramethylguanidinium azide (1.40 g, 8.85 mmol, previously dried under vacuum for 36 hrs over P$_2$O$_5$) in dichloromethane (10 ml) was added via a canula. After a further 5 minutes at −10° C., the mixture was allowed to warm to room temperature and stirred for 30 minutes. Saturated sodium bicarbonate solution was added and the product was extracted into n-hexane. The extracts were washed with saturated sodium bicarbonate solution, dried over anhydrous magnesium sulphate, filtered and concentrated in vacuo.

Purification by flash chromatography On Silica gel (eluting with ethyl acetate/n-hexane mixtures) gave the title compound (D10) as a crispy yellow foam.

IR νmax (thin film): 3422, 2945, 2905, 2870, 2090, 1731,1500,1454,1409,1375,1303,1235,1187,1100,1072,10-00, 896,855,830,725,665 cm⁻¹.

δH 400 MHz ((CD₃)₂CO): 7.88 (2H,d,J 7.5Hz), 7.70 (2H,d,J 7.4Hz), 7.43 (2H,t,J 7.4Hz), 7.34 (2H,t,J 7.4Hz), 6.55–6.10 (12H. series of m). 6.05 (1H,dd,J 15.3, 6.1Hz), 5.51 (1H,dd,J 14.8, 9.5Hz). 5.34 (1H,d.J 9.8Hz). 4.74 (1H,s), 4.74–4.63 (2H,m), 4.48 (1H,dd,J 10.4, 6.5Hz), 4.34 (1H,dd,J 10.4, 6.5Hz). 4.30–4.20 (2H,m), 4.16–4.06 (2H,m), 4.00 (1H,m), 3.96 (1H,d,J 2.6Hz), 3.88–3.80 (2H,m), 3.77 (2H,d,J 2.6Hz), 3.73–3.58 (3H, series of m), 3.48 (1H,t,J 9.0Hz), 3.36 (1H,dq,J 8.5, 6.2Hz), 3.13 (3H,s), 2.59 (1H,dd, A of ABX system, J 17, 5.6Hz), 2.53 (1H,dd, B of ABX system, J 17, 7.1Hz) 2.44 (1H,m), 2.27 (1H,m), 2.15 (1H,dd,J 12 3,4.5Hz), 2.08–1.45 (14H, series of m), 1.26 (3H,d,J 6.1Hz), 1.18 (3H,d,J 6.0Hz), 1.10–0.85 (87H, series of m), 0.78–0.53 (54H, series of m) ppm.

Mass spectrum: FAB (3-NOBA/sodium matrix) Observed mass 2220, calculated mass for C₁₁₇H₂₁₂N₄O₁₇-Si₉Na⁺, 2220.

DESCRIPTION 11

N-(9-Fluorenylmethoxycarbonyl)-16-decarboxy-16-iodomethyl-13-O-methyl-3,5,8,9,11,15,35,2′,4′-nona-O-triethylsilylamphotericin B (D11)

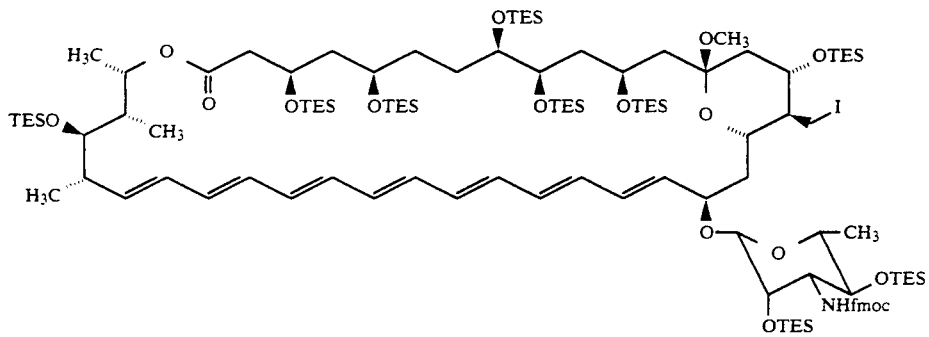

N (9-Fluorenylmethoxycarbonyl)-16-decarboxy-16-hydroxymethyl-13-O-methyl-3,5,8,9,11,15,35,2′,4′-nona-O -triethylsilyl amphotericin B (D5) (524 mg, 0.24 mmol) dissolved in dichloromethane (3 ml), was cooled to −10° C. and treated with pyridine (98 μl, 1.21 mmol). This mixture was treated with a solution of trifluoromethanesulphonic anhydride (93 μl, 0.56 mmol) in dichloromethane (3 ml) added via canula. After stirring for 5 minutes, a solution of tetra-n-butylammonium iodide (579 mg, 1.57 mmol) in dichloromethane (3 ml) was added via canula and the mixture then allowed to reach room temperature. After 50 minutes the mixture was washed with saturated sodium hydrogen carbonate solution, diluted with n-hexane and washed with saturated sodium sulphite solution. The organic extract was dried over anhydrous magnesium sulphate, filtered, concentrated in vacuo and then purified by flash chromatography on silica-gel using 10% ethyl acetate in n-hexane as the eluent to give the title compound (D11). δH 400 MHz (d₆-acetone): 7.87 (2H, d, J 7.5 Hz), 7.69 (2H, d, J 7.4 Hz), 7.43 (1H, d, J 7.4 Hz), 7.41 (1H, d, J 7.5 Hz), 7.35 (1H, d, J 7.4 Hz), 7.33 (1H, d, 7.4 Hz), 6.58–6.00 (13H, series of m), 5.52 (1H, dd, J 14.8 and 9.5 Hz), 5.28 (1H, d, J 9.8 Hz), 4.87 (1H,s), 4.80–4.65 (2H,m), 4.48 (1H, dd, J 10.5 and 6.4 Hz), 4.35 (1H, dd, J 10.5 and 6.3 Hz), 4.30–4.20 (2H,m), 4.19–3.95 (4H,m), 3.84 (1H, dd, J 8.8 and 2.5 Hz), 3.81–3.60 (5H,m), 3.55–3.35 (3H,m), 3.15 (3H,s), 2.60–2.53 (2H,m), 2.44 (1H,m), 2.27 (1H,m), 2.18 (1H, dd, J 12.3 and 4.6 Hz), 2.10–1.45 (14H, series of m), 1.26 (3H, d, J 6.0 Hz), 1.08 (3H, d, J 6.0 Hz), 1.14–0.82 (87H, complex), 0.82–0.55 (54H, complex) ppm.

Mass spectrum: FAB (3-NOBA/sodium matrix) observed mass 2305.5 - calculated mass for C₁₁₇H₂₁₂O₁₇-Si₉NINa⁺, 2305.3 Rf 0.35 (silica) - 10% ethyl acetate in n-hexane.

DESCRIPTION 12

N-(9-Fluorenylmethoxycarbonyl)-16-cyanomethyl-16-decarboxy-13-O-methyl-3,5,8,9,11,15,35,2′,4′-nona-O-triethylsilylamphotericin B (D12)

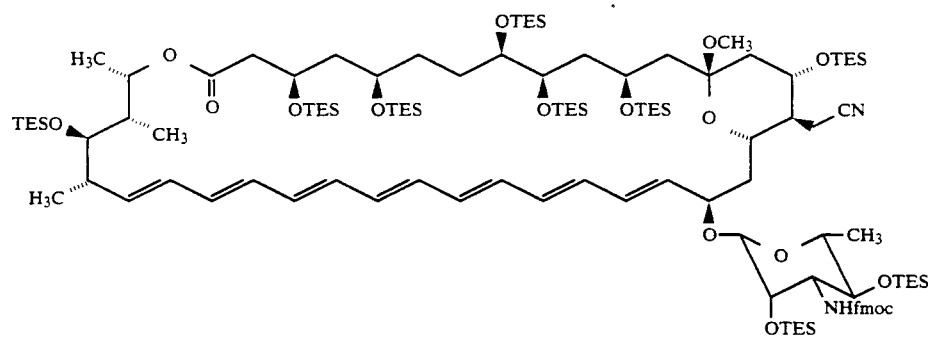

N-(9-Fluorenylmethoxycarbonyl)-16-decarboxy-16-hydroxymethyl-13-O-methyl-3,5,8,9,11,15,35,2′,4′-nona-O-triethylsilylamphotericin B (D5) (469 mg, 0.22 mmol) dissolved in dichloromethane (6 ml) was cooled to −10° C. and treated with pyridine (105 μl, 1.30 mmol). This mixture was treated with a solution of trifluoromethanesulphonic anhydride (102 μl, 0.60 mmol) in dichloromethane (3 ml) added via canula. After stirring for 5 minutes a solution of tetra-n- butylammonium cyanide (529 mg, 1.97 mmol) in dichloromethane (3 ml) was added via canula and the mixture then allowed to warm to room temperature. After 15 minutes the mixture was washed with saturated sodium hydrogen carbonate solution and diluted with n-hexane. The separated organic phase was dried over anhydrous magnesium sulphate, filtered, concentrated in vacuo and purified by flash chromatography on silica-gel eluting with 10% ethyl acetate in n-hexane to give the title compound (D12).

cludes 7.9 (2H,d), 7.7 (2H,d), 7.4 (4H,m), 6.6–6.0 (14H, complex), 5.5 (1H,dd) 5.4 (1H,d), 3.2 (3H,s) and 2.1 (3H,s) ppm.

Mass spectrum: FAB (3-NOBA/Na matrix) observed mass MNa+ 2236 (±1), calculated for $C_{119}H_{215}NO_{19}Si_9Na$, 2237.

DESCRIPTION 14

N-(9-Fluorenylmethoxycarbonyl)-16-azidomethyl-16-decarboxy-13-O-methylamphotericin B (D14)

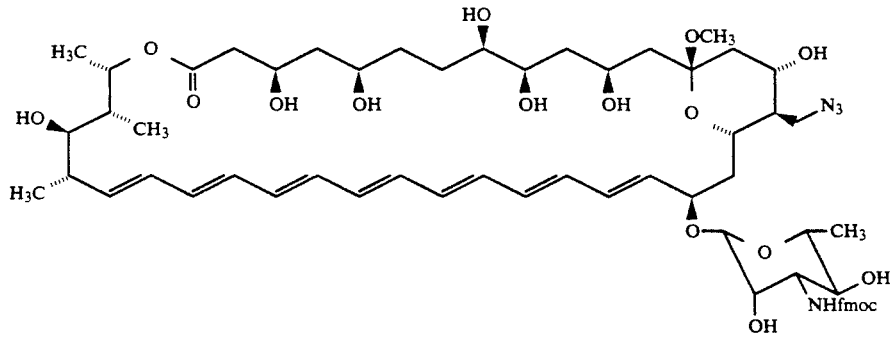

$\delta^{13}C$ 67.80 MHz ($d_6$-acetone); includes 118.70 (1C), 16.11 (1C) ppm.

Mass spectrum FAB (3-NOBA/sodium matrix) observed mass 2204-calculated mass for $C_{118}H_{212}O_{17}Si_9N_2Na^+$, 2204.4. Rf 0.34 (silica) - 10% ethyl acetate in n-hexane.

DESCRIPTION 13

N-(9-Fluorenylmethoxycarbonyl)-16-acetoxymethyl-16-decarboxy-13-O-methyl-3,5,8,9,11,15,35,2′,4′-nona-O-triethylsilylamphotericin B (D13)

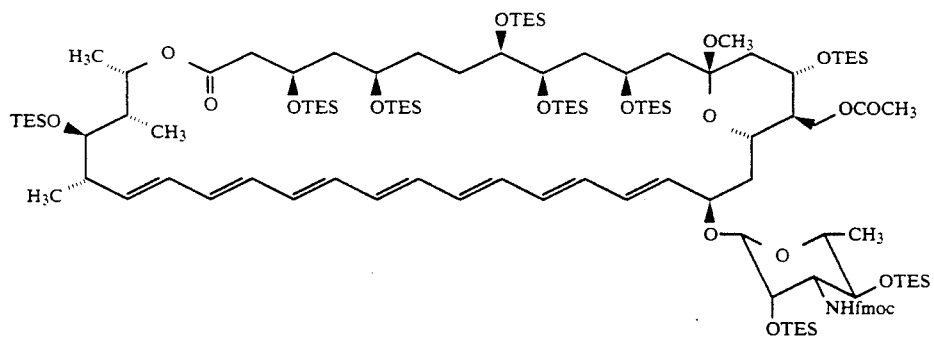

The alcohol of Description 5 (0.37 g, 0.17 mmol) in dry dichloromethane (20 ml) under a nitrogen atmosphere at ambient temperature was treated with dry pyridine (0.055 ml, 0.68 mmol) and 4-dimethylaminopyridine (0.021 g, 0.17 mmol) followed by acetic anhydride (0.077 ml, 0.68 mmol). After 1 hour more pyridine (0.027 ml) and acetic anhydride (0.037 ml) were added. The solution was stirred overnight at room temperature then evaporated in vacuo and the residue dissolved in diethyl ether (25 ml). The ether solution was washed with 0.1N hydrochloric acid, water, dilute sodium hydrogen carbonate solution, brine, then dried over magnesium sulphate and filtered. The filtrate was evaporated to give a yellow gum.

The crude product was purified by column chromatography on silica-gel eluting with 1% diethyl ether in dichloromethane to give the title compound (D13) as a yellow foam (0.27 g). $\delta H$ 270 MHz ($d^6$-acetone) in- A mixture of the title azidomethyl derivative of Description 10 (2.324 g, 1.06 mmol) and hydrogen fluoride-pyridine solution (42 ml of a solution of 11.4 g of hydrogen fluoride-pyridine and 80 ml of pyridine made up to 200 ml with dry tetrahydrofuran) in methanol (20 ml)/tetrahydrofuran (20 ml) was stirred in a plastic bottle at room temperature for 20 hrs. The mixture was added to diethyl ether/n-hexane (2 L,1:1) and the precipitated solid was collected by filtration, washed with 7% aqueous disodium hydrogen phosphate, water and dried under suction. Purification by flash chromatography on silica gel (eluting with the lower phase of a 3:1:1 mixture of chloroform:methanol:0.880 ammonia solution) gave the title compound (D14) as a bright yellow powder.

$\delta H$ 400MHz ($d_4$-methanol/$d_5$-pyridine 1:1): 7.84 (2H,d,J 7.5Hz) 7.71 (2H,t,J 7.1Hz), 7.40 (2H,t,J 7.4Hz), 7.30 (2H,t,J 7.3Hz), 6.57–6.27 (12H, series of m), 6.11 (1H,dd,J 14.3, 7.2Hz), 5.62 (1H,dd,J 14.2, 9.5Hz), 5.46 (1H,m), 4.92 (1H,s), 4.78 (1H,m), 4.47 (1H,m), 4.38 (2H,d,J 7.3Hz), 4.28 (1H,d,J 2.7Hz), 4.26–4.15 (3H,m), 4.14–4.04 (2H,m), 4.02–3.90 (2H,m), 3.87–3.73 (3H,m), 3.61 (1H,dq,J 9.1, 6.1Hz), 3.52 (1H,m), 3.47 (1H,dd,J 9.2, 1.9Hz), 3.26 (3H,s), 2.60–2.47 (3H,m, including 1H,dd, at 2.52, J 16.6, 8.9Hz), 2.40 (1H,dd,J 16.6, 3.3Hz), 2.35 (1H,m), 2.10–1.55 (14H, series of m), 1.49

(3H,d,J 6.0Hz), 1.34 (3H,d,J 6.3Hz), 1.25 (3H,d,J 6.5Hz), 1.15 (3H,d,J 7.1Hz) ppm.

Mass spectrum: FAB (3-NOBA/sodium matrix) Observed mass 1193, calculated mass for $C_{63}H_{86}N_4O_{17}Na^+$, 1193.6.

DESCRIPTION 15

N-(9-Fluorenylmethoxycarbonyl)-16-decarboxy-16-phenylthiomethyl-13-O-methylamphotericin B (D15)

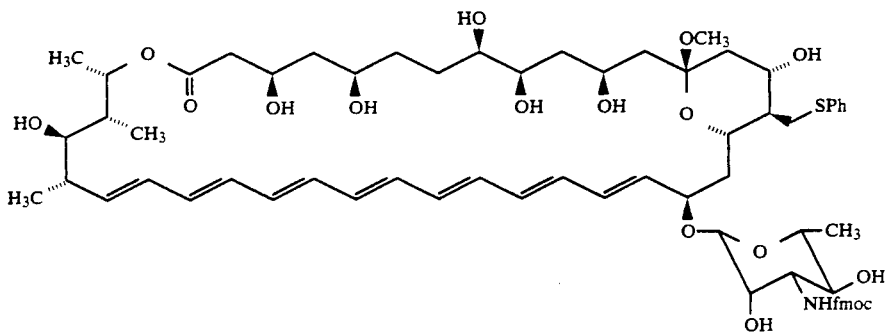

N-(9-Fluorenylmethoxycarbonyl)-16-decarboxy-16-hydroxymethyl-13-O-methylamphotericin B (D8) (0.67 g, 0.58 mmol) dissolved in dry tetrahydrofuran (35 ml) was treated with diphenyl disulphide (1.44 g, 6.61 mmol) followed by tri-n-butylphosphine (1.65 ml, 6.61 mmol) at 0° C. for 6.25 hours. The mixture was stored at −15° C. overnight, and then at 0° C. for a further 5.5 hours. The reaction mixture was concentrated and poured into (1:1) diethylether:hexane (2 liters). The yellow product was filtered, washed with diethyl ether and dried under vacuum.

The crude material thus obtained was purified by column chromatography on normal phase silica-gel eluting with the lower phase of chloroform, methanol and concentrated ammonia solution (10:1:1). The title compound (D15) was obtained as a yellow solid.

δH 270MHz [($C_5D_5N:CD_3OD(1:1)$)] 7.86 (2H,d,J 7.4Hz), 7.72 (2H,m), 7.60–7.10 (9H, complex), 6.60–6.20 (12H, complex), 6.13 (1H,dd,J 14.5 and 7.5Hz), 5.64 (1H,m), 4.02 (1H,s), 4.84 (1H,m), 4.48 (1H,m), 4.41 (2H,d,J 7.2Hz), 4.50–4.15 (5H, complex), 4.10 (1H,m), 3.98 (1H,m), 3.90–3.35 (7H, complex), 3.29 (3H,s), 2.65–2.30 (5H, complex), 2.15–1.50 (14H, complex), 1.46 (3H,d,J 5.8Hz), 1.34 (3H,d,J 6.1Hz), 1.25 (3H,d,J 5.8Hz), 1.16 (3H,d,J 6.9Hz) ppm. One signal masked by solvent.

Mass Spectrum FAB (3-NOBA sodium matrix) observed mass 1260 - calculated mass for $C_{69}H_{91}NO_{17}SNa$, 1260.6.

HPLC: Reverse phase ODS 5μ 250×4.6 mm column; eluent 80% methanol - 20% pH 3.5 phosphate buffer - 1 mlmin$^{-1}$; detection wavelength 350 nm; Retention time: 16.0 minutes.

DESCRIPTION 16

N-(9-Fluorenylmethoxycarbonyl)-16-decarboxy-16-phenythiomethylamphotericin B (D16)

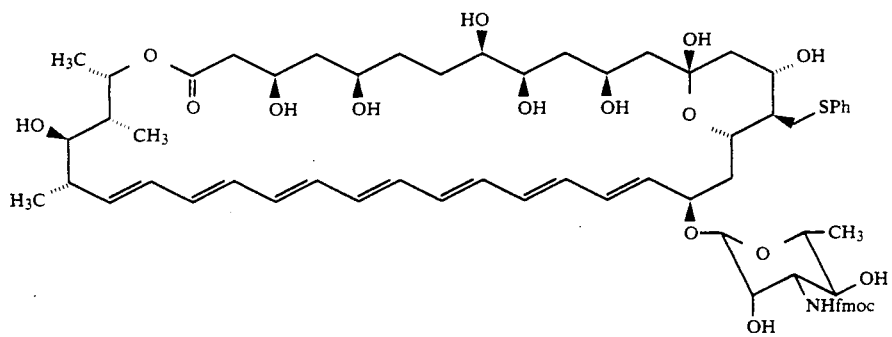

N-(9 Fluorenylmethoxycarbonyl)-16-decarboxy-16-phenylthiomethyl-13-O-methylamphotericin B (D15) (0.15 g, 0.12 mmol) dissolved in tetrahydrofuran:water (2:1) (6 ml) was treated with 10-camphorsulphonic acid (0.07 g, 0.28 mmol) to lower the pH of the reaction mixture to ca.pH 2. After 0.7 hours the reaction mixture was treated with triethylamine (0.05 ml, 0.36 mmol), concentrated and poured into water (700 ml). The yellow product, N-(9-fluorenylmethoxycarbonyl)-16-decarboxy-16-phenylthiomethylamphotericin B was collected by centrifugation, washed with water and dried under vacuum. The crude material thus obtained was purified by column chromatography on normal phase silica-gel eluting with the lower phase of chloroform, methanol and concentrated ammonia solution (10:1:1) to give the title compound (D16).

DESCRIPTION 17

N-(9-Fluorenylmethoxycarbonyl)-16-decarboxy-16-iodomethyl-13-O-methylamphotericin B (D17)

DESCRIPTION 18

N-(9-Fluorenylmethoxycarbonyl)-16-decarboxy-16-iodomethylamphotericin B (D18)

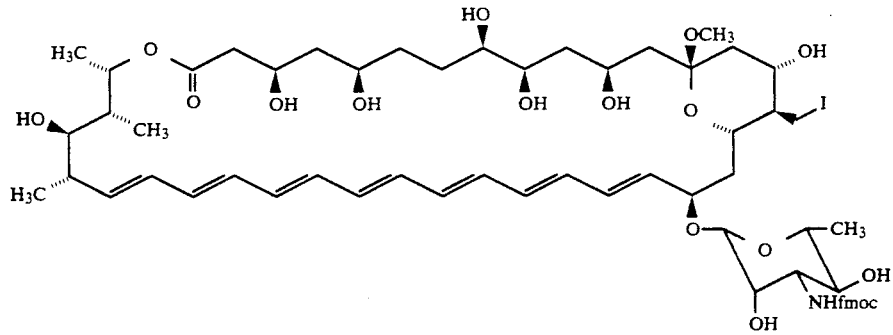

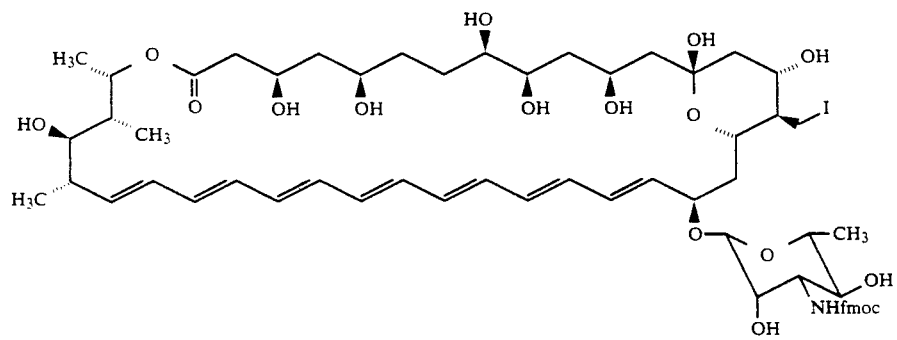

N-(9-Fluorenylmethoxycarbonyl)-16-decarboxy-16-iodomethyl-13-O-methyl-3,5,8,9,11,15,35,2',4'-nona-O-triethylsilylamphotericin B (D11) (206 mg, 0.09 mmol), methanol (1 ml), and hydrogen fluoride-pyridine solution (3.65 ml of a solution of 11.4 g of hydrogen fluoride-pyridine and 80 ml of pyridine made up to 200 ml in tetrahydrofuran) were stirred overnight at room temperature under a nitrogen atmosphere in a plastic bottle. The mixture was poured into diethyl ether (0.2L) and the precipitated solid was filtered and washed with diethyl ether. The crude material was purified by flash chromatography on silica-gel eluting with 8:1; dichloromethane:methanol to give the title compound (D17) as a yellow solid.

Mass spectrum: FAB (3-NOBA/sodium matrix) observed mass 1279-calculated mass for $C_{63}H_{86}O_{17}$·NINa$^+$, 1278.5. HPLC: Reverse phase ODS 5μ 250×4.6 mm column; eluent 80% methanol - 20% pH 3.5 phosphate buffer - 1 mlmin$^{-1}$; detection wavelength 350 nm; retention time: 9.8 minutes.

N-(9-Fluorenylmethoxycarbonyl)-16-decarboxy-16-iodomethyl-13-O-methylamphotericin B (D17) (66 mg, 0.05 mmol), dissolved in a 2:1 mixture of tetrahydrofuran:water (3 ml), was treated with pyridinium p-toluenesulphonate (90 mg, 0.36 mmol) at room temperature. After 2 hours, triethylamine (70 μl, 0.5 mmol) was added, and the mixture was concentrated and poured into water (100 ml). The product was washed with water and purified by chromatography on silica-gel using dichloromethane/methanol mixtures as the eluent to give the title compound (D18) as a yellow solid.

Mass spectrum: FAB (3-NOBA/sodium matrix) observed mass 1264 calculated mass for $C_{62}H_{84}O_{17}$·NINa$^+$, 1264. HPLC: Reverse phase ODS 5μ 250×4.6 mm column; eluent 80% methanol - 20% pH 3.5 phosphate buffer - 1 mlmin$^{-1}$; detection wavelength 350 nm; retention time: 18.8 minutes.

DESCRIPTION 19

N-(9-Fluorenylmethoxycarbonyl)-16-cyanomethyl-16-decarboxy-13-O-methylamphotericin B (D19)

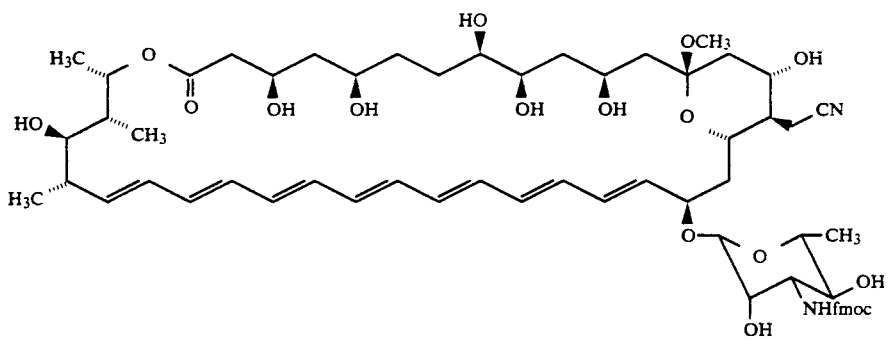

N-(9-Fluorenylmethoxycarbonyl)-16-cyanomethyl-16-decarboxy-13-O-methyl-3,5,8,9,11,15,35,2',4'-nona- O -triethyl silylamphotericin B (D12) (314 mg, 0.14 mmol), methanol (1.5 ml), and hydrogen fluoride-pyridine solution (5.75 ml of a solution of 11.4 g of hydrogen fluoride-pyridine and 80 ml of pyridine made up to 200 ml in tetrahydrofuran) were stirred overnight under a nitrogen atmosphere at room temperature in a plastic bottle. The mixture was poured into a 3:2 mixture of diethyl ether: n-hexane (0.45 L). The precipitated product was filtered and dried in vacuo to give the title compound (D19) as a yellow solid.

Mass spectrum: FAB (3-NOBA/sodium matrix) observed mass 1177-calculated mass for $C_{64}H_{86}O_{17}N_2Na^+$, 1177.6.

HPLC: Reverse phase ODS 5μ 250×4.6 mm column; eluent 83% methanol - 17% pH 3.5 phosphate buffer -1 mlmin$^{-1}$; detection wavelength 350 nm; retention time: 5.7 minutes. Rf 0.45 (silica) - 11% methanol in dichloromethane.

DESCRIPTION 20

N-(9-Fluorenylmethoxycarbonyl)-16-cyanomethyl-16-decarboxyamphotericin B (D20)

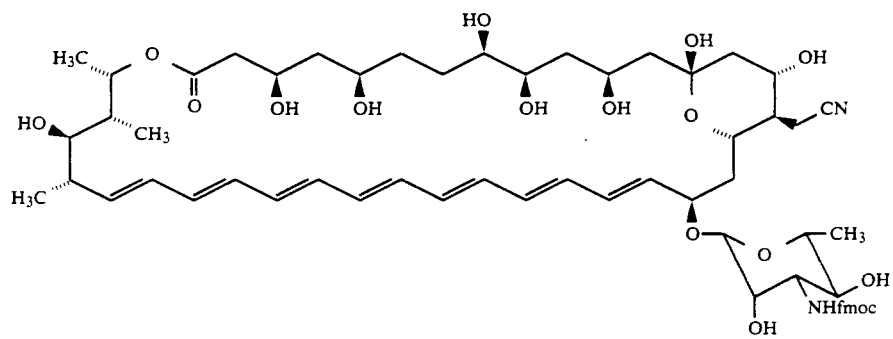

N-(9-Fluorenylmethoxycarbonyl)-16-cyanomethyl-16-decarboxy-13-O-methyl amphotericin B (D19) (103 mg, 0.09 mmol) dissolved in a 2:1 mixture of tetrahydrofuran: water (7 ml) was treated with pyridinium p-toluenesulphonate (125 mg, 0.50 mmol) at room temperature. After 2 hours, triethylamine (85 μl, 0.60 mmol) was added and the mixture was poured into water (20 ml). The precipitate was isolated by centrifugation and purified by medium pressure chromatography on silicagel using the lower phase of chloroform:methanol:0.880 ammonia mixtures to give the title o compound (D20) as a yellow solid.

DESCRIPTION 21

N-(9-Fluorenylmethoxycarbonyl)-16-acetoxymethyl-16-decarboxy-13-O-methylamphotericin B (D21)

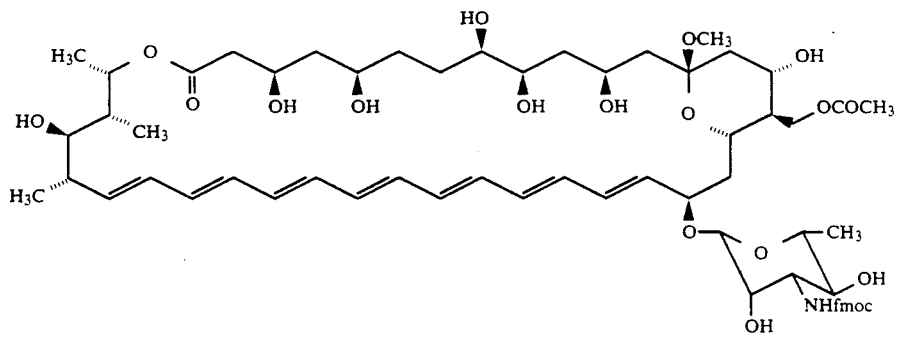

The compound of Description 13 (0.27 g, 0.12 mmol) was dissolved in dry tetrahydrofuran (4 ml) in a plastic bottle under a nitrogen atmosphere at 0° C. Dry methanol (1 ml) was added, followed by hydrogen fluoride pyridine (5 ml of a solution made up with 11.4 g of hydrogen fluoride.pyridine in 80 ml pyridine made up to 200 ml with dry tetrahydrofuran). The reaction mixture was allowed to warm to ambient temperature and was stirred for 24 hours. The solution was poured into a mixture of diethyl ether and n-hexane (2:1, 200 ml total volume). The precipitated solid was collected by centrifugation, was washed with diethyl ether, dissolved in methanol and the solution evaporated to give the title compound (D21) as a yellow powder (0.13 g).

$\delta$H 270 MHz (1:1 $d^4$-methanol/$d^5$-pyridine) includes 7.8 (2H,d) 7.7 (2H,d), 7.3 (4H,m), 6.6–6.2 (13H, complex), 6.1 (1H,dd), 5.6 (1H,dd), 4.9 (1H,s), 3.3 (3H,s), 2.1 (3H,s), 1.5 (3H,d), 1.3 (3H,d), 1.2 (3H,d) and 1.1 (3H,d) ppm.

Mass spectrum: FAB (3-NOBA/Na matrix) observed mass MNa+ 1210, calculated for $C_{65}H_{89}NO_{19}Na$, 1210.

DESCRIPTION 22

N-(9-Fluorenylmethoxycarbonyl)-16-acetoxymethyl-16-decarboxyamphotericin B (D22)

DESCRIPTION 23

Allyl succinimidyl carbonate. (D23)

A mixture of N-hydroxysuccinimide (4.78 g, 0.042 mol) and allyl chloroformate (5.0 g, 4.40 ml, 0.042 mmol) in dry tetrahydrofuran (60 ml) was cooled to 0° C. under nitrogen. A solution of triethylamine (4.2 g, 5.78 ml, 0.042 mol) in tetrahydrofuran (20 ml) was added dropwise over 20 minutes. After completion of the addition, the mixture was stirred at room temperature for 4 hours, and then filtered and concentrated. Ethyl acetate (200 ml) was added and the resulting solution was washed sequentially with water (3×), saturated sodium bicarbonate solution and water (3×). Drying (MgSO4) and removal of the solvent in vacuo gave the title compound as a clear, colourless oil. (D23).

$\delta$H 270 MHz (CDCl$_3$): 5.96 (1H, ddt, J 17.3, 10.4, 6.1Hz), 5.45 (1H, ddd, J 17.3, 2.7, 1.4Hz), 5.38 (1H, ddd, J 10.2, 2.2, 1.1Hz), 4.79 (2H, ddd, J 6.1, 1.4, 1.1Hz), 2.84 (4H,s).

Mass spectrum: FAB (Glycerol) observed mass 200, calculated for $C_8H_9NO_5H^+$ 200; High resolution: observed 200.0560, calculated 200.0559.

DESCRIPTION 24

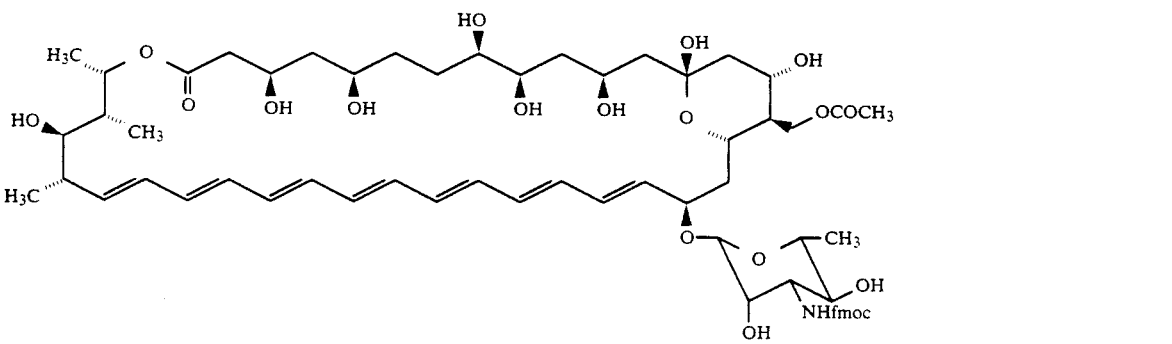

N-(9-Fluorenylmethoxycarbonyl-16-acetoxymethyl-16-decarboxy-13-O-methylamphotericin B (D21) (0.17

N-Allyloxycarbonyl-16-azidomethyl-16-decarboxy-13-O-methylamphotericin B (D24)

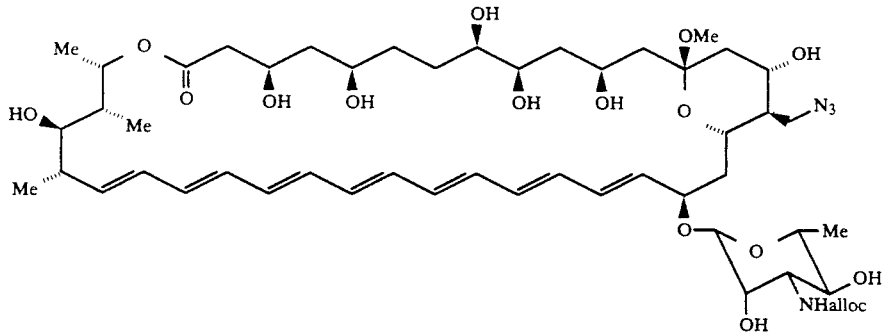

g, 0.14 mmol) was dissolved in tetrahydrofuran (4 ml) and water (1 ml) and was treated with pyridinium p-toluene sulphonate (0.26 g, 1.0 mmol). After 0.8 hours triethylamine (0.16 ml, 1.2 mmol) was added and the mixture was stirred for 0.1 hour. The crude reaction mixture was poured into water (250 ml) and the precipitated solid collected by filtration and dried in vacuo. The product was purified by column chromatography on silica-gel eluting with 0–10% methanol/ethyl acetate mixtures to give the title compound (D22).

The amine of Example 2 (482 mg, 0.508 mmol), allyl succinimidyl carbonate (202 mg, 1.02 mmol) and pyridine (60.3 mg, 0.062 ml, 0.762 mmol) were stirred together in dimethyl formamide (5ml)/methanol (1.5 ml) at room temperature under nitrogen. After 2 hours, the mixture was added to ether/hexane (5:1, 1L). The precipitated product was collected by filtration, washed with diethyl ether and then dissolved from the filter with methanol. Removal of the methanol in vacuo gave the title compound as a yellow powder (D24).

Mass spectrum: FAB (Thiodiethanol/sodium) Observed mass 1055, calculated mass for $C_{48}H_{76}N_4O_{15}Na^+$ 1055.5.

DESCRIPTION 25

3'-N-allyloxycarbonyl-16-aminomethyl-16-decarboxy-13-O-methylamphotericin B (D25)

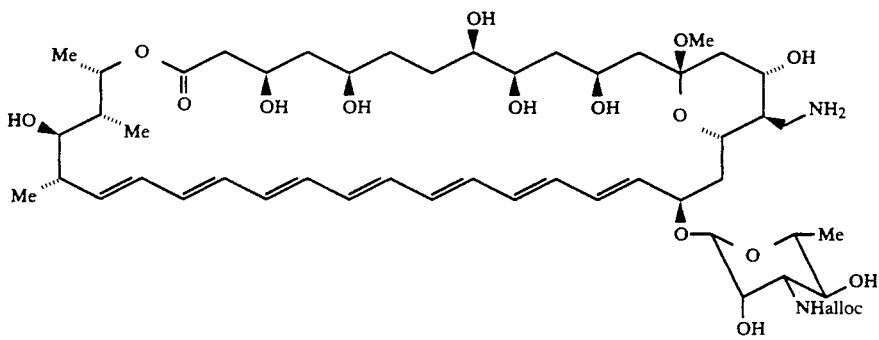

The azide of Description 24 (484 mg, 0.469 mmol) and triethylphosphine (289 mg, 0.361 ml, 2.44 mmol) were stirred in tetrahydrofuran (10 ml) at room temperature under nitrogen. After 30 minutes, water (0.5 ml) was added and the mixture was refuluxed for 30 minutes. The solvent was removed and the residue was chromatographed on silica gel (eluting with the lower phase of chloroform/methanol/0.880 ammonia mixtures) to give the title compound as a yellow powder. (D25)

IR $\nu$max (KBr disc): 3421 (broad), 2933, 1706, 1640, 1517, 1384, 1313, 1186, 1130, 1069, 1010 cm$^{-1}$.

$\delta$H 400 MHz (D$_4$-methanol/D$_5$-pyridine 1:1): 6.58–6.27 (12H, series of m), 6.12 (1H, dd, J 14.3, 7.7Hz), 5.95 (1H, m), 5.58 (1H, dd, J 14.4, 9.7Hz), 5.52 (1H,m), 5.31 (1H, partially masked by solvent), 5.15 (1H, dd, J 10.5, 1.2Hz), 4.83 (1H,s), 4.73 (1H,m), 4.60 (2H,m), 4.47 (1H, tt, J 9.3, 3.2Hz), 4.25 (1H, dd, J 10.7, 4.7Hz), 4.21 (1H,m), 4.18 (1H, d, J 2.8 Hz), 4.02–3.92 (3H,m), 3.82 (1H,m), 3.71 (1H,m), 3.58–3.40 (3H, series of m), 3.29 (1H, dd, J 12.9, 2.3Hz), 3.25 (3H,s), 2.90 (1H, dd, J 12.9, 7.1Hz), 2.56 (1H,m), 2.51 (1H, dd, J 16.5, 9.0Hz), 2.41 (1H,m), 2.40 (1H, dd, J 16.6, 3.3Hz), 2.29 (1H,m), 2.14–1.92 (5H, series of m), 1.83–1.55 (9H, series of m), 1.45 (3H, d, J 6.1Hz), 1.35 (3H, d, J 6.4Hz), 1.24 (3H, d, J 6.5Hz), 1.16 (3H, d, J 7.2Hz) ppm.

Mass spectrum: FAB (Thiodiethanol/sodium) Observed mass 1029, calculated mass for $C_{52}H_{82}N_2O_{17}Na^+$ 1029.5.

DESCRIPTION 26

N-Allyloxycarbonyl-16-acetamidomethyl 16-decarboxy-13-O-methylamphotericin B (D26)

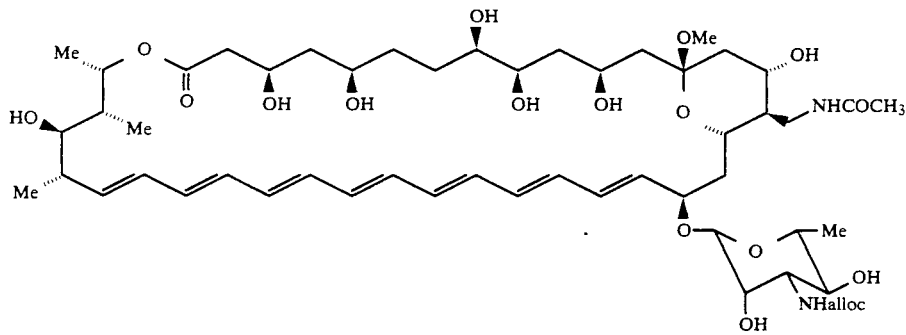

A solution of the amine of Description 25 (100 mg, 0.100 mmol) in dimethyl sulphoxide (1 ml)/methanol (3 drops) was stirred at room temperature and treated with acetic anhydride (0.014 ml, 15.4 mg, 0.150 mmol). After 1 hour, the mixture was diluted with methanol (1 ml) and added to ether (400 ml). The precipitated product was collected by filtration, washed with ether and then dissolved from the filter with methanol. Removal of the solvent in vacuo gave the title compound. (D26)

Mass spectrum: FAB (Thiodiethanol/sodium). Observed mass 1071, calculated mass for $C_{54}H_{84}N_2O_{18}Na^+$ 1071.6.

DESCRIPTION 27

N-(9-Fluorenylmethoxycarbonyl)-16-decarboxy-16-(diethoxyphosphoramido)methyl-13-O-methyl-3,5,8,9,11, 15,35,2',4'-nona-O-triethylsilylamphotericin B. (D27)

DESCRIPTION 28

N-(9-Fluorenylmethoxycarbonyl)-16-decarboxy-16-methyl-13-O-methyl-3,5,8,9,11,15,35,2$^1$,4$^1$-nona-O-triethylsilylamphotericin B (D28)

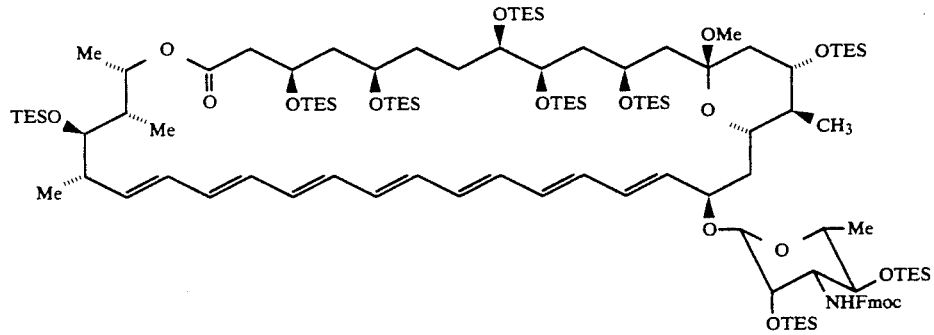

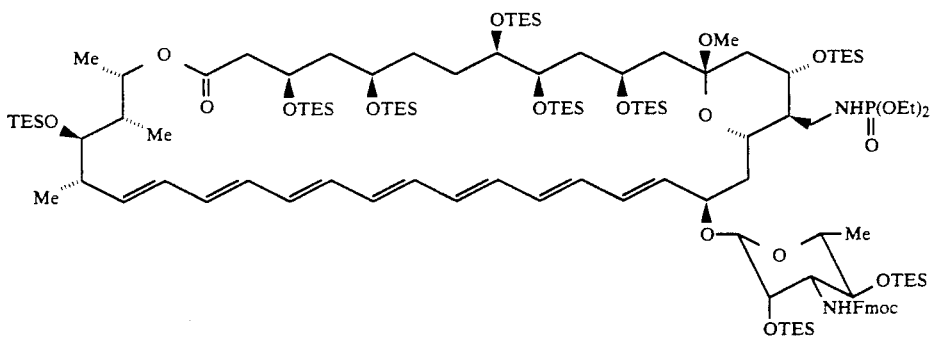

N (9-Fluorenylmethoxycarbonyl)-16-decarboxy-16-

A mixture of the azide of Description 10 (300 mg, 0.136 mmol) and triethylphosphite (226 mg, 0.233 ml, 1.36 mmol) in dry tetrahydrofuran (8 ml) was refluxed under nitrogen for 3 hours. Water (0.1 ml) was added and the mixture was refluxed for a further 1 hour. The solvent was removed in vacuo and the crude product was purified by flash chromatography on silica gel (eluting with ethyl acetate/hexane mixtures) to give the title compound as a yellow glass (D27).

δH 400 MHz (D6-Acetone): 7.87 (2H, d, J 7.5Hz), 7.69 (2H, d, J 7.4Hz), 7.42 (2H, t, J 7.4Hz), 7.34 (2H, t, J 7.4Hz), 6.52–6.09 (12H, series of m), 6.04 (1H, dd, J 15.5, 6.0Hz), 5.51 (1H, dd, J 14.8, 9.6Hz), 5.30 (1H, d, J 9.8Hz), 4.86 (1H,s), 4.78–4.61 (2H, m), 4.47 (1H, dd, J 10.4, 6.5Hz), 4.34 (1H, dd, J 10.4, 6.5Hz), 4.28–4.22 (2H,m), 4.14–3.90 (8H, series of m), 3.94 (1H, d, J 2.7Hz), 3.85–3.54 (6H, series of m), 3.50–3.42 (2H,m), 3.11 (3H,s), 2.60–2.39 (3H,m), 2.29 (1H,m), 2.15 (1H,m), 2.11 (1H, dd, J 12.2, 4.4Hz), 2.05–1.42 (13H, series of m), 1.31–1.24 (9H, m, including 3H, d, J 6.9Hz at 1.29), 1.18 (3H, d, J 6.0Hz), 1.10–0.88 (87H, series of m), 0.78–0.57 (54H, series of m).

Mass spectrum: FAB (NoBA/sodium) Observed mass 2330, calculated mass for $C_{48}H_{76}N_4O_{15}Na^+$ 2330.4.

iodomethyl-13-O-methyl-3,5,8,9,11,15,35,2$^1$,4$^1$-nona-O-triethylsilylamphotericin B (D11) (1.233 g, 0.54 mmol) dissolved in tetrahydrofuran (18 ml), was cooled to −10° C. and treated with lithium triethylborohydride (6.5 ml of a 1M tetrahydrofuran solution, 6.50 mmol). After 20 minutes the mixture was washed with saturated ammonium chloride solution. The organic extract was dried over anhydrous magnesium sulphate, filtered, concentrated in vacuo and then purified by flash chromatography on silica gel using 9% ethyl acetate in n-hexane as the eluent to give the title compound. (D28)

δH 270 MHz (D6-acetone): 7.88 (2H, d, J 7.4Hz), 7.70 (2H, d, J 7.4Hz), 7.45 (1H, d, J 7.4Hz), 7.42 (1H, d, J 7.2Hz), 7.36 (1H, d, J 7.4Hz), 7.33 (1H, d, J 7.4Hz), 6.65–6.00 (13H, series of m), 5.50 (1H, dd, J 15.1 and 9.6Hz), 5.41 (1H, d, J 9.9Hz), 4.70 (1H,s), 4.69–4.57 (2H,m), 4.48 (1H, dd, J 10.3 and 6.5Hz), 4.35 (1H, dd, J 10.4 and 6.3Hz), 4.30–4.19 (2H,m), 4.11 (1H,m), 4.00 (1H,m) 3.91 (1H, d, J 2.8Hz), 3.86 (1H,m), 3.81–3.53 (5H,m), 3.48 (1H, t, J 8.9Hz), 3.35 (1H,m), 3.11 (3H,s), 2.58 (2H,m), 2.45 (1H,m), 2.30–1.30 (16H, series of m), 1.25 (3H, d, J 6.1Hz), 1.18 (3H, d, J 6.1Hz), 1.14–0.82 (90H, complex), 0.82–0.52 (54H, complex) ppm.

Rf 0.36 (silica) - 10% ethyl acetate in n-hexane.

DESCRIPTION 29

N-(9-Fluorenylmethoxycarbonyl)-16-decarboxy-16-methyl-13-O-methylamphotericin B (D29)

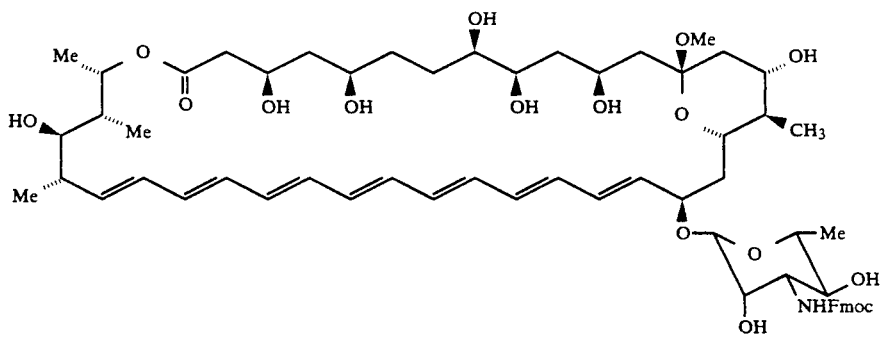

A mixture of the title 16-methyl derivative of Descripton 28 (516 mg, 0.239 mmol) and hydrogen fluoride-pyridine solution (6.5 ml of a solution of 11.4 g of hydrogen fluoride-pyridine and 80 ml of pyridine made up to 200 ml with dry tetrahydrofuran) in methanol (2 ml)/tetrahydrofuran (2 ml) was stirred in a plastic bottle at room temperature for 20 hrs. The mixture was added to diethyl ether/n-hexane (2L, 1:1) and the preciptated solid was collected by filtration, washed with diethyl ether and dried. Purification by flash chromatography on silica gel (eluting with the lower phase of a 10:1:1 mixture of chloroform:methanol:0.880 ammonia solution) gave the title compound as a yellow powder. (D29)

Mass spectrum: FAB (Thiodiethanol/sodium matrix) observed mass 1152.5, calculated mass for $C_{63}H_{87}O_{17}NNa^+$, 1152.6. HPLC: Reverse phase ODS 5μ 250×4.6 mm column; eluent 82% methanol - 18% pH 3.5 phosphate buffer - 1 ml.min$^{-1}$; detection wavelength 350 nm; retention time: 6.7 minutes.

EXAMPLE 1

16-Azidomethyl-16-decarboxyamphotericin B (E1)

water and dried to give a yellow powder. This product was dissolved in dimethyl sulphoxide (10 ml)/methanol (2 ml) and treated with piperidine (0.040 g, 0.046 ml, 0.465 mmol). After stirring at room temperature for 1 hr another batch of piperidine (0.015 ml) was added and stirring was continued for a further 30 minutes. The mixture was diluted with methanol (8 ml) and added to diethyl ether (1L). The precipitated product was collected by filtration, washed with diethyl ether and dried. Purification by flash chromatography on silica gel (eluting with the lower phase of a 4:1:1 mixture of chloroform:methanol: 0.880 ammonia solution) gave the title compound (E1) as a yellow powder. IR νmax (KBr disc): 3470 (broad), 2910,2085,1705,1445, 1175,1055,1005,880,845cm$^{-1}$.

δH 400MHz (d4-methanol/d5-pyridine 1:1): 6.66-6.26 (13H, series of m), 5.61 (1H,dq,J 6.3,2.0Hz), 5.49 (1H,dd,J 14.6, 10.1Hz), 4.84 (1H,s), 4.72 (1H,m), 4.64-4.53 (2H,m), 4.44 (1H,tt,J 9.7, 2.7Hz), 4.23 (1H,dt,J 10.7, 4.6Hz), 4.16 (1H,d,J 3.1Hz), 3.94 (1H,m), 3.88-3.82 (2H,m), 3.78 (1H,dd,J 12.8, 2.6Hz), 3.50-3.39 (3H,m), 3.36 (1H,dd,J 9.5, 1.8Hz), 2.81 (1H,dd,J 9.3, 3.1Hz), 2.60-2.46 (2H,m), 2.47 (1H,dd,J 16.9, 9.7Hz, A of ABX system), 2.34 (1H,dd,J 16.8, 2.7Hz, B of ABX system), 2.30 (1H,dd,J 12.2, 14.7Hz), 2.09 (1H,m), 2.03-1.45 (13H, Series of m), 1.44 (3H,d,J 5.7Hz), 1.34 (3H,d,J 6.4Hz), 1.23 (3H,d,J 6.4Hz), 1.15 (3H,d,J 7.2Hz) ppm.

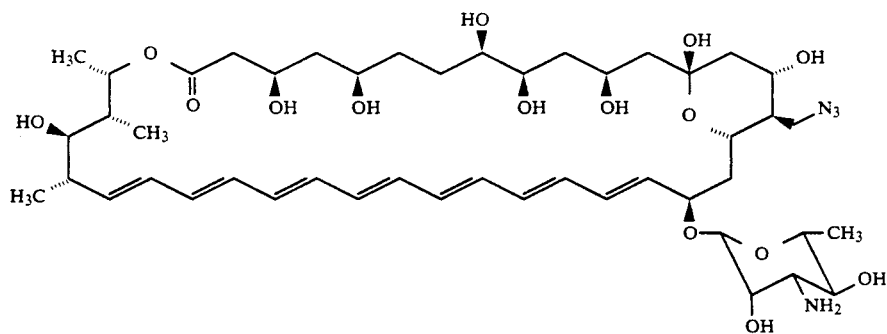

The title azide of Description 14 (0.424 g, 0.362 mmol) and pyridinium p-toluenesulphonate (0.357 g, 1.420 mmol) were stirred in tetrahydrofuran (15 ml)/water(5 ml) at room temperature. After 1 hr, triethylamine (0.187 g, 0.257 ml, 1.850 mmol) was added and the tetrahydrofuran was removed in vacuo. The aqueous residue was added to water (800 ml) and the precipitated product was collected by filtration, washed with Mass spectrum FAB (Thiodiethanol/sodium matrix) Observed mass 957.5, calculated mass for $C_{47}H_{74}N_4O_{15}Na^+$, 957.5.

EXAMPLE 2

16-Azidomethyl-16-decarboxy-13-O-methylamphotericin B (E2)

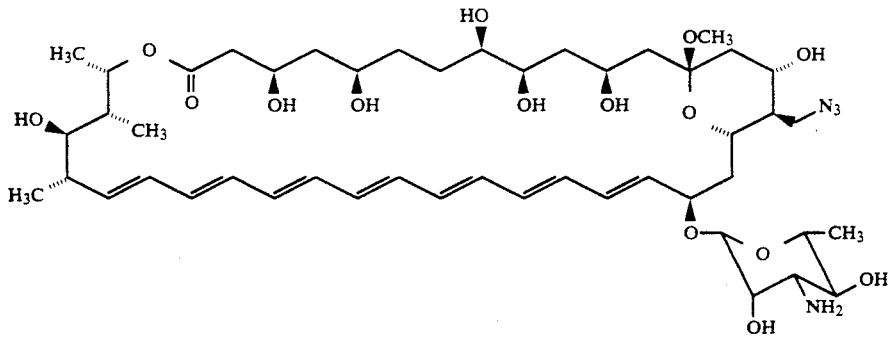

The title compound of Description 14 (0.391 g, 0.334 mmol) and piperidine (0.057 g, 0.066 ml, 0.668 mmol) were stirred at room temperature in dimethylsulphoxide (5 ml)/methanol (0.5 ml). After 30 minutes the mixture was diluted with methanol (3 ml) and added to diethyl ether (1L). The precipitated product was collected by filtration, washed with diethyl ether and dried. Purification by column chromatography on silica gel (eluting with the lower phase of chloroform:methanol: 0.880 ammonia mixtures) gave the title compound (E2) as a yellow powder.

IR νmax (KBr disc): 3460 (broad), 2930,2110,1720,1450, 1370,1305,1135,1060,1010,885,850cm$^{-1}$.

δH 400MHz (d4-methanol/d5-pyridine 1:1):6.56–6.26 (12H, series of m), 6.09 (1H,dd,J 14.4, 7.2Hz), 5.61 (1H,dd,J 14.3, 9.5Hz), 5.45 (1H,m), 4.84 (1H,s), 4.78 (1H,m), 4.44 (1H,m), 4.21–4.13 (3H,m), 4.05 (1H,m), 3.96 (1H,m), 3.94 (1H,dd,J 12.7, 3.5Hz), 3.82–3.76 (2H,m), 3.52–3.36 (4H,m), 3.25 (3H,s), 2.80 (1H,m), 2.56–2.45 (3H,m, including 1H,dd,J 16.6, 8.8Hz at 2.50), 2.39 (1H,dd,J 16.6, 3.4Hz), 2.37 (1H,m), 2.05–1.55 (14H, series of m), 1.44 (3H,d,J 5.7Hz), 1.33 (3H,d,J 6.4Hz), 1.23 (3H,d,J 6.5Hz), 1.14 (3H,d,J 7.1Hz).ppm.

Mass spectrum: FAB (Thiodiethanol/sodium matrix) Observed mass 971.5, calculated mass for $C_{48}H_{76}N_4O_{15}Na^+$, 971.5.

EXAMPLE 3

16-Aminomethyl-16-decarboxy-13-O-methylamphotericin B (E3)

tetrahydrofuran (10 ml) was stirred at room temperature for 1 hr. More water (0.040 ml) was added and the mixture was refluxed for 8 hrs. Concentration, followed by purification by a combination of column chromatography and preparative TLC on silica gel (eluting with the lower phase of a 2:1:1 mixture of chloroform:methanol:0.880 ammonia solution) gave the title compound (E3).

IR νmax (KBr disc): 3380 (broad), 2920,1720,1580,1440, 1375,1315,1060,1010,885,850.

δH 400MHz (d4-methanol/d5-pyridine 1:1):6.58–6.28 (12H, series of m), 6.13 (1H,dd,J 14.1, 7.6Hz), 5.59 (1H,dd,J 14.2, 9.8Hz), 5.51 (1H,m), 4.83 (1H,s), 4.76 (1H,m), 4.47 (1H,tt,J 9.3, 3.2Hz), 4.33–4.15 (3H,m, including 1H,d,J 2.9Hz at 4.18), 4.02–3.91 (2H,m), 3.81 (1H,m), 3.57–3.40 (4H,m, partially masked by solvent peaks), 3.36 (1H,m), 3.25 (3H,s), 2.98 (1H,dd,J 12.9, 7.3Hz), 2.92 (1H,dd,J 9.3, 2.8Hz), 2.56 (1H,m), 2.52 (1H,dd,J 16.7, 9.1Hz, A of ABX system), 2.46 (1H,dd,J 12.7, 4.6Hz), 2.40 (1H,dd,J 16.6, 3.3Hz, B of ABX system), 2.32 (1H,m), 2.16–1.94 (5H, series of m), 1.84–1.62 (8H, series of m), 1.59 (1H, dt, J 14.0, 3.3Hz), 1.44 (3H,d,J 5.8Hz), 1.35 (3H,d,J 6.4Hz), 1.25 (3H,d,J 6.5Hz), 1.16 (3H,d,J 7.2Hz) ppm.

Mass spectrum: FAB (3-NOBA/sodium matrix) Observed mass 945.4, calculated mass for $C_{48}H_{78}N_2O_{15}Na^+$, 945.5.

Method B

A mixture of the title azide of Example 2 (0.101 g, 0.104 mmol), propane-1,3-dithiol (0.113 g, 0.104 ml, 1.04 mmol) and triethylamine (0.105 g, 0.145 ml, 1.04 mmol) in dry methanol (4 ml) was stirred at room temperature under nitrogen. After 53 hrs the mixture was added to diethyl ether/n-hexane (500 ml, 1:1). The precipitated product was collected by centrifugation, washed with

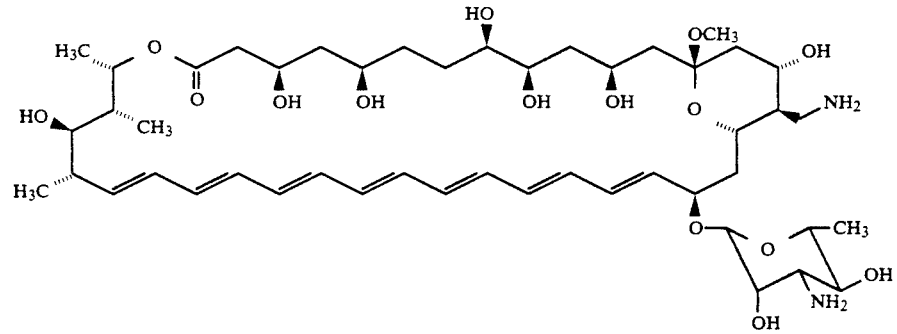

Method A

A mixture of the title azide of Example 2 (0.095 g, 0.098 mmol), triphenylphosphine (0.128 g, 0.49 mmol) and water (0.040 ml) (0.018 g, 0.018 ml, 1.00 mmol) in diethyl ether and dried. Purification by column chromatography on silica gel (eluting with the lower phase of a 2:1:1 mixture of chloroform:methanol:0.880 ammonia solution) gave the title compound (E3).

Method C

The title azide of Example 2 (0.120 g, 0.124 mmol) and triethylphosphine (0.073 g, 0.092 ml, 0.620 mmol) were stirred in dry tetrahydrofuran (12 ml) at room temperature under nitrogen. After 30 minutes, water (0.2 ml) was added and the mixture was refluxed for 1 hr. Concentration and purification as in Method B gave the title compound (E3).

EXAMPLE 4

6-Decarboxy-16-phenylthiomethylamphotericin B (E4)

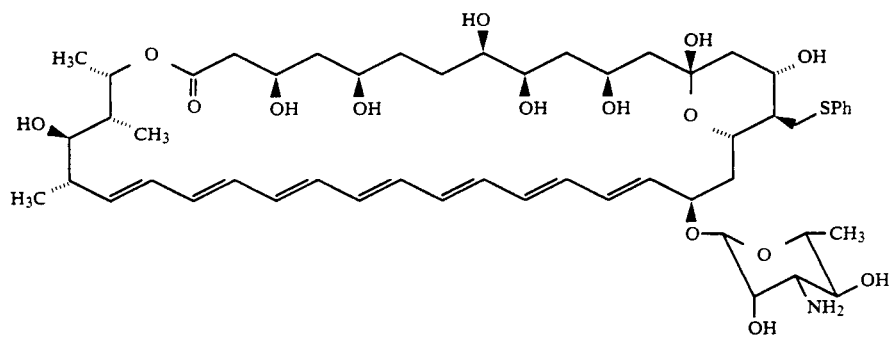

The purified N (9-fluorenylmethoxycarbonyl)-16-decarboxy-16-phenylthiomethylamphotericin B (D16) (60 mg, 0.053 mmol) dissolved in dimethyl sulphoxide:-methanol (3.5:1) (1 ml) was treated with piperidine (0.011 ml, 0.111 mmol). After 1 hour and addition of methanol (1 ml) the reaction mixture was poured into diethyl ether (300 ml). The title product, 16-decarboxy-16-phenythiomethylamphotericin B (E4) was collected by centrifugation, washed with diethyl ether and dried under vacuum.

δH 400MHz [($C_5D_5N:CD_3OD(1:1)$)] 7.50 (2H,m), 7.33 (2H,m), 7.17 (1H,m), 6.68–6.28 (11H, complex), 6.39 (1H,m), 6.35 (1H,m), 5.50 (1H,dd,J 14.8 and 10.1Hz), 4.85 (1H,s), 4.79 (1H,m), 4.70–4.60 (2H,m), 4.46 (1H, tt,J 9.7 and 2.9Hz), 4.40 (1H,dt,J 11.1 and 4.7Hz), 4.20 (1H,d,J 3.0Hz), 4.0 (1H,m), 3.87 (1H,m), 3.55–3.35 (6H, complex, partially masked by solvent peaks), 2.70 (1H,dd,J 14.6 and 5.4Hz), 2.63 (1H,dd,J 9.4 and 3.1Hz), 2.57 (1H,m), 2.49 (1H,dd,J 16.8 and 9.7Hz, A of ABX system), 2.36 (1H,dd,J 16.9 and 2.8Hz, B of ABX system), 2.34 (1H,dd,J 11.9 and 4.9Hz), 2.20–1.45 (14H, complex), 1.42 (3H,d,J 5.9Hz), 1.36 (3H,d,J 6.4Hz), 1.25 (3H,d,J 6.4Hz), 1.17 (3H,d,J 7.1Hz) ppm. Mass spectrum FAB (3-NOBA sodium matrix) observed mass 1024 - calculated mass for $C_{53}H_{79}NO_{15}SNa$, 1024.5.

HPLC: Reverse phase ODS 5μ 250×4.6 mm column; eluent 83% methanol - 17% pH 3.5 phosphate buffer - 1 mlmin$^{-1}$; detection wavelength 350 nm; Retention time: 11.5 minutes.

EXAMPLE 5

16-Decarboxy-16-iodomethylamphotericin B (E5)

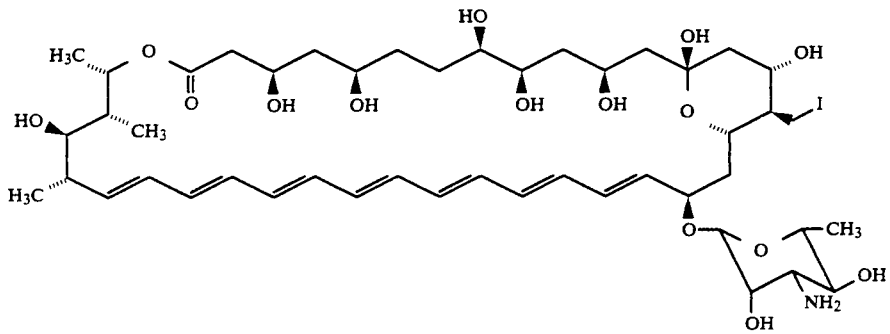

The compound of Description 18 (58 mg, 0.04 mmol), dissolved in a 3.5:1 mixture of dimethylsulphoxide/methanol (1.5 ml), was treated with piperidine (10μl, 0.09 mmol). After 2 hours the reaction mixture was poured into diethyl ether (0.2L) and the precipitated solid filtered and washed with diethyl ether. The crude material was purified by flash chromatography on silica-gel eluting with the lower phase of chloroform:methanol:0.880 ammonia mixtures to give the title compound (E5) as a yellow solid.

δH 400 MHz ($d_4$-methanol/$d_5$-pyridine): 6.70–6.20 (13H, series of m), 5.62 (1H,m), 5.51 (1H, dd, J 14.8 and 10.1 Hz), 4.99 (1H,s), 4.80 (1H,m), 4.63 (1H,m), 4.55 (1H,m), 4.47 (1H,m), 4.39 (1H, d, J 3.1 Hz), 4.10 (1H,m), 4.08–3.91 (2H,m), 3.88 (1H,m), 3.60–3.33 (5H, series of m), 2.91 (1H,m), 2.62–2.30 (5H, series of m), 2.20–1.40 (14H, complex), 1.47 (3H, d, J 5.5 Hz), 1.36 (3H, d, J 6.4 Hz), 1.25 (3H, d, J 6.4 Hz), 1.17 (3H, d, J 7.1 Hz) ppm.

Mass spectrum: FAB (3-NOBA/sodium matrix) observed mass 1042-calculated mass for $C_{47}H_{73}4O_{15}NINa^+$, 1042.4.

HPLC: Reverse phase ODS 5μ 250×4.6 mm column; eluent 80% methanol -20% pH 3.5 phosphate buffer - 1 mlmin$^{-1}$; detection wavelength 350nm; retention time: 12.4 minutes.

EXAMPLE 6

6-Cyanomethyl-16-decarboxy-13-O-methylamphotericin B (E6)

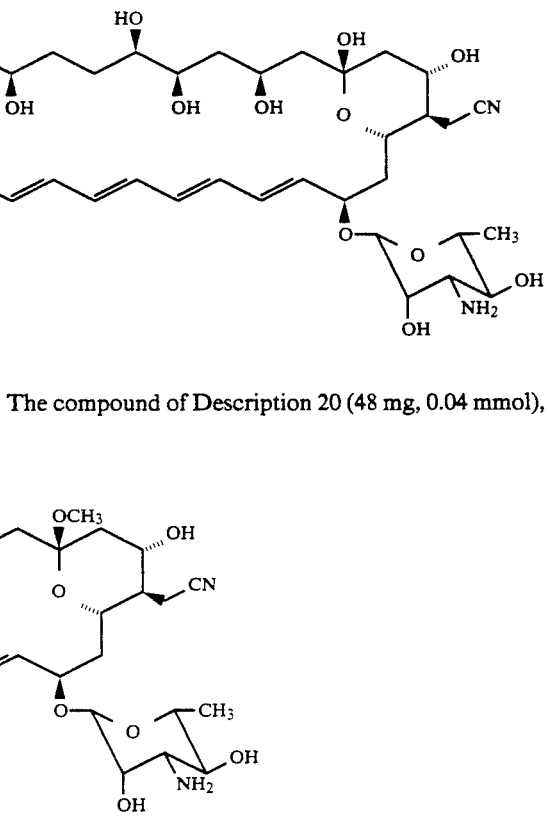

N (9-Fluorenylmethoxycarbonyl)-16-cyanomethyl-16-decarboxy-13-O-methylamphotericin B (D19) (63 mg, 0.05 mmol) dissolved in a 3.5:1 mixture of dimethyl sulphoxide/methanol (1.5 ml) was treated with piperidine (11μl, 0.11 mmol). After 1 hour the reaction mixture was precipitated by pouring into diethyl ether (0.4 L), filtered and washed with diethyl ether. The crude material was purified by flash chromatograpy on silica-gel eluting with the lower phase of chloroform: methanol:0.880 ammonia mixtures to give the title compound (E6) as a yellow solid.

δH 400 MHz (d4-methanol/d5-pyridine, 1:1) 6.60–6.25 (12H, series of m), 6.14 (1H,m), 5.66 (1H, dd, J 14.3 and 9.5 Hz), 5.60–5.30 (1H, obscured by solvent peak), 4.93 (1H,s), 4.83 (1H,m), 4.47 (1H,m), 4.26 (1H, d, J 3.2 Hz), 4.30–4.10 (3H, series of m), 3.98 (1H,m), 3.82 (1H,m), 3.60–3.35 (4H, series of m), 3.27 (3H,s), 3.15 (1H, dd, J 17.5 and 3.9 Hz), 2.96–2.80 (2H,m), 2.70–2.35 (5H, series of m), 2.12–1.53 (14H, complex), 1.45 (3H, d, J 5.6 Hz), 1.34 (3H, d, J 6.3 Hz), 1.25 (3H, d, J 6.5 Hz), 1.15 (3H, d, J 7.1 Hz) ppm.

Mass spectrum: FAB (3-NOBA/sodium matrix) observed mass 955-calculated mass for $C_{49}H_{76}N_2O_{15}Na^+$, 955.5.

HPLC: Reverse phase ODS 5μ 250×4.6 mm column; eluent 80% methanol -20% pH 3.5 phosphate buffer - 1 mlmin$^{-1}$; detection wavelength 350 nm; retention time: 7.1 minutes. IR νmax (KBr disc): 3400 (broad), 2925, 2260, 1720, 1635, 1440, 1378, 1319, 1134, 1067, 1012, 887, 850 and 795cm$^{-1}$.

EXAMPLE 7

16-Cyanomethyl-16-decarboxyamphotericin B (E7)

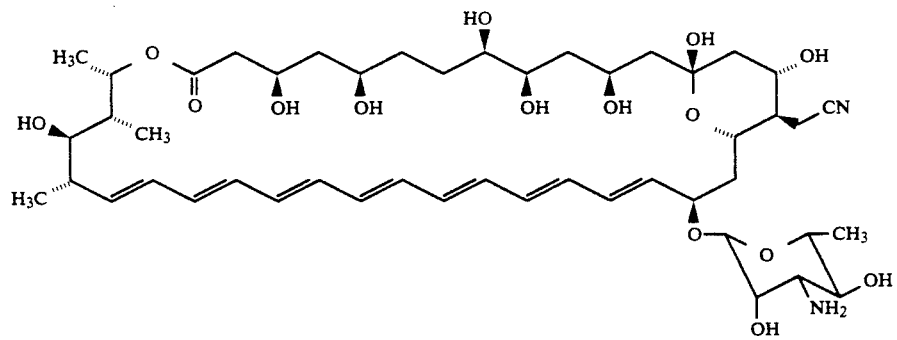

The compound of Description 20 (48 mg, 0.04 mmol), dissolved in a 3.5:1 mixture of dimethyl sulphoxide/methanol (1.25 ml) was treated with piperidine (9μl, 0.09 mmol). After 1.25 hours the reaction mixture was precipitated by pouring into diethyl ether (0.4L), filtered and washed with diethyl ether. The crude material was purified by flash chromatograpy on silica-gel eluting with the lower phase of chloroform:methanol:0.880 ammonia mixtures to give the title compound (E7).

δH 400 MHz (d4-methanol/d5-pyridine, 1:1) 6.70–6.25 (13H, series of m), 5.64 (1H,m), 5.50 (1H,m), 4.90 (1H,s), 4.74 (1H,m), 4.71–4.59 (2H,m), 4.47 (1H,m), 4.29 (1H, d, J 3.0 Hz), 4.24 (1H, dt, J 10.7 and 4.6 Hz), 3.96 (1H,m), 3.86 (1H,m), 3.55–3.40 (3H,m), 3.37 (1H,m), 3.07 (1H, dd, J 17.5 and 4.1 Hz), 2.95–2.84 (2H,m), 2.62–2.26 (5H, series of m), 2.23–1.40 (14H, complex), 1.43 (3H, d, J 5.6 Hz), 1.36 (3H, d, J 6.4 Hz), 1.25 (3H, d, J 6.4 Hz), 1.17 (3H, d, J 6.9 Hz) ppm.

Mass spectrum: FAB (3-NOBA/sodium matrix) observed mass 941 calculated mass for $C_{48}H_{74}N_2O_{15}Na^+$, 941.5.

HPLC: Reverse phase ODS 5μ 250×4.6 mm column; eluent 83% methanol -17% pH 3.5 phosphate buffer - 1 mlmin$^{-1}$; detection wavelength 350 nm; retention time: 8.8 minutes.

IR νmax (KBr disc): 3400 (broad), 3012, 2931, 2247, 1717, 1630, 1448, 1383, 1323, 1269, 1183, 1129, 1108, 1066, 1012, 887, 850 and 795cm$^{-1}$.

EXAMPLE 8

16-Acetoxymethyl-16-decarboxyamphotericin B (E8)

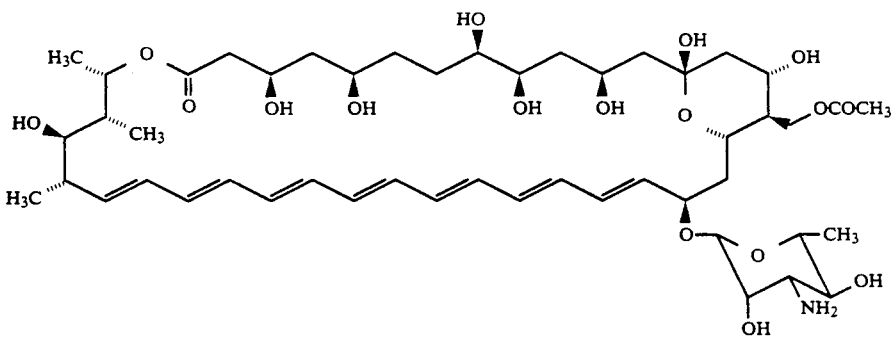

N-(9-Fluorenylmethoxycarbonyl)-16-acetoxymethyl-16-decarboxyamphotericin B (D22) (0.07 g, 0.063 mmol) was dissolved in a mixture of dimethyl sulphoxide and methanol (3.5:1, 3 ml total volume) and then treated with piperidine (0.012 ml, 0.12 mmol). After 0.6 hour methanol (0.5 ml) was added and the solution poured into diethyl ether (200 ml). The precipitate was filtered, dissolved in a mixture of methanol and tetrahydrofuran (1:1, 5 ml) and evaporated in vacuo. The product was purified by column chromatography on silicagel eluting with 0-40% methanol in dichloromethane mixtures to give the title compound (E8).

$\delta$H 270MHz (1:1 d$^4$-methanol/d$^5$-pyridine) includes 6.7-6.2 (14H,m), 4.85 (1H,s), 4.2 (1H,d), 2.05 (3H,s) ppm.

Mass spectrum:FAB (thiodiethanol/sodium matrix) observed mass MNa$^+$ 974, calculated for C$_{49}$H$_{77}$NO$_{17}$Na, 974.

EXAMPLE 9

16-Acetamidomethyl-16-decarboxyamphotericin B (E9)

tor to give the N-allyloxycarbonyl derivative of the title compound.

This product was stirred in dimethylformamide (4 ml) with PdCl$_2$(PPh$_3$)$_2$ (7.6 mg, 0.011 mmol) and acetic acid (15.3 mg, 0.015 ml, 0.255 mmol) at 0° C. under nitrogen.

Tri n-butyl tin hydride (74 mg, 0.069 ml, 0.255 mmol) was added dropwise over 4 minutes. After completion of the addition the mixture was stirred at 0° C. for 30 minutes and then added to diethyl ether (400 ml). The precipitated product was collected by filtration and washed with diethyl ether. Purification by flash chromatography on silica gel (eluting with the lower phase of a 3:1:1 mixture of chloroform:methanol:0.880 ammonia solution) gave the title compound as a yellow powder. (E9)

IR $\nu$max (KBr disc): 3380 (broad), 2930, 1717, 1635, 1554, 1448, 1377, 1318, 1180, 1069, 1011, 886, 850, 793cm$^{-1}$.

$\delta$H 400MHz (D$_4$-methanol/D$_5$-pyridine 1:1): 6.69-6.62 (2H,m), 6.56-6.28 (11H, series of m), 5.63 (1H,m), 5.50 (1H, dd, J 14.8, 10.1Hz), 4.82 (1H,s), 4.66-4.59 (2H,m), 4.52-4.42 (2H,m), 4.18 (1H,m), 4.17 (1H, d, J 3.1Hz), 3.98-3.92 (2H,m), 3.84 (1H,m), 3.51-3.33 (5H, series of m), 2.90 (1H, dd, J 9.2, 3.1Hz),

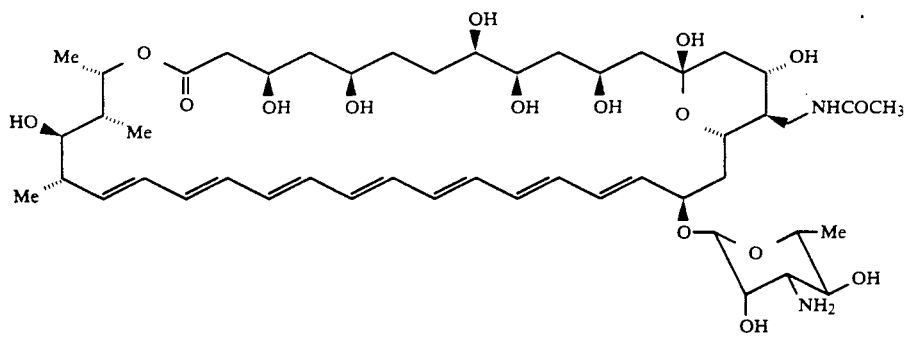

A mixture of the title compound of Description 26 (98.5 mg, 0.094 mmol) and pyridinium p-toluenesulphonate (112 mg, 0.450 mmol) in tetrahydrofuran (3 ml)/water (1 ml) was stirred at room temperature for 40 minutes. Triethylamine (62 mg, 0.085 ml, 0.610 mmol) was added and the tetrahydrofuran was removed on the rotary evaporator. The aqueous residue was added to water (100 ml), and the precipitated product was collected by filtration and washed with water. The yellow powder was dissolved from the filter with tetrahydrofuran and the solvent was removed on the rotary evaporator.

2.61-2.47 (2H,m), 2.49 (1H, dd, J 16.8, 9.6Hz), 2.35 (1H, dd, J 16.7, 2.8Hz), 2.25 (1H, dd, J 12.0, 4.6Hz), 2.18-1.46 (17H, series of m, including 3H,s at 2.04), 1.39 (3H, d, J 5.8Hz), 1.35 (3H, d, J 6.4Hz), 1.24 (3H, d, J 6.4Hz), 1.17 (3H, d, J 7.2Hz) ppm.

Mass spectrum: FAB (Thiodiethanol/sodium) Observed mass 973, calculated mass for C$_{49}$H$_{78}$N$_2$O$_{16}$Na$^+$ 973.5.

EXAMPLE 10

16-Decarboxy-16-(p-toluenesulphonamidomethyl)-amphotericin B (E10)

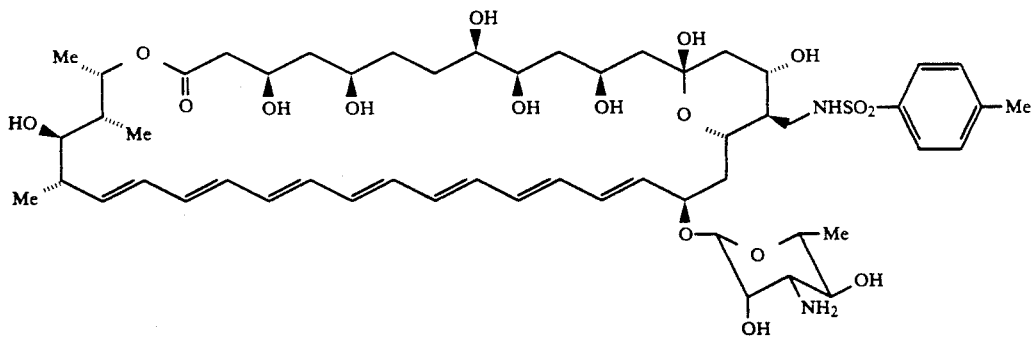

A mixture of the amine of Description 25 (102 mg, 0.101 mmol), p-toluenesulphonyl chloride (29 mg, 0.152 mmol) and anhydrous potassium carbonate (42 mg, 0.303 mmol) in dry dimethyl formamide (4 ml) was stirred at room temperature under nitrogen. Further batches of p-toluenesulphonyl chloride (10.5 mg after 30 minutes reaction) and potassium cabonate (a spatula tip after 45 minutes) were added to complete the reaction. After stirring for 1 hour in total, the mixture was added to diethyl ether (400 ml). The precipitated solid was collected by filtration and washed with diethyl ether and water. Purification by flash chromatography on silica gel (eluting with chloroform/methanol 6:1) gave a yellow solid (74.2 mg).

This product was stirred at room temperature in tetrahydrofuran (3 ml)/water (1 ml) with pyridinium p-toluenesulphonate (80 mg, 0.320 mmol).After 40 minutes, triethylamine (42 mg, 0.058 ml, 0.416 mmol) was added and the tetrahydrofuran was removed on the rotary evaporator. The aqueous residue was added to water (200 ml) and the precipitated product was collected by filtration, washed with water and then dissolved from the filter with tetrahydrofuran. Removal of the solvent in vacuo gave the N-allyloxycarbonyl derivative of the title compound (70.4 mg).

This product was stirred in dimethylformamide (4 ml) with $PdCl_2(PPh_3)_2$ (5.9 mg, 0.008 mmol) and acetic acid (11 mg, 0.011 ml, 0.183 mmol) at 0° C. under nitrogen. Tri n-butyl tin hydride (53 mg, 0.049 ml, 0.183 mmol) was added dropwise over 3 minutes. After stirring at 0° C. for 30 minutes more tri-n-butyl tin hydrde (53 mg, 0.049 ml, 0.183 mmol) was added dropwise. The mixture was stirred for a further 15 minutes at 0° C. and then added to diethyl ether (300 ml). The precipated product was collected by filtration, washed with diethyl ether and then dissolved from the filter with tetrahydrofuran/methanol. Removal of the solvent in vacuo and purification by flash chromatography on silica gel (eluting with the lower phase of chloroform/methanol/0.880 ammonia solution mixtures) gave the title compound as a yellow powder. (E10)

IR νmax (KBr disc): 3426 (broad), 2925, 1700, 1635, 1528, 1446, 1384, 1322, 1157, 1093, 1069, 1012, 885, 850, 814cm$^{-1}$.

δH 400Mz (D$_4$-methanol/D$_5$-pyridine 1:1): 7.92 (2H, d, J 8.2Hz), 7.31 (2H, d, J 8.1Hz), 6.69–6.60 (2H,m), 6.57–6.27 (11H, series of m), 5.64 (1H,m), 5.51 (1H, dd, J 14.7, 10.2Hz), 5.12 (1H,s), 4.77 (1H,m), 4.67–4.54 (2H,m), 4.47 (1H,m), 4.34 (1H, d, J 2.9Hz), 4.16 (1H,m), 3.97 (1H,m), 3.86 (1H,m), 3.66–3.56 (2H,m), 3.47–3.36 (2H,m), 3.34 (2H, d, J 3.6Hz), 3.20 (1H, dd, J 9.1, 2.9Hz) 2.78 (1H,m), 2.57 (1H,m), 2.50 (1H, dd, J 16.8, 9.7Hz), 2.36 (1H, dd, J 17.0, 2.4Hz), 2.32 (3H,s), 2.26 (1H, dd, J 12.1, 4.6Hz), 2.13 (1H,m), 2.04–1.47 (13H, series of m), 1.46 (3H, d, J 5.5Hz), 1.36 (3H, d, J 6.4Hz), 1.25 (3H, d, J 6.3Hz), 1.17 (3H, d, J 7.1Hz).

Mass spectrum: FAB (Thiodiethanol/sodium) Observed mass 1086, calculated for $C_{54}H_{82}N_2O_{17}$-SNa$^+$1085.5.

EXAMPLE 11

16-Decarboxy-16-(diethoxyphosphoramido)methyl-amphotericin B (E11)

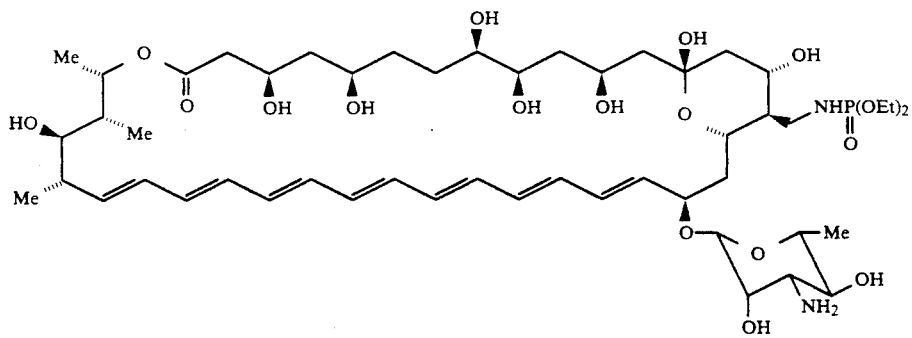

A mixture of the title compound of Description 27 (259 mg, 0.112 mmol) and hydrogen fluoride-pyridine solution (4.5 ml of a solution of 11.4 g of hydrogen fluoride-pyridine and 80 ml of pyridine made up to 200 ml with dry tetrahydrofuran) in tetrahydrofuran (4 ml) was stirred overnight at room temperature in a plastic bottle. Methanol (1 ml) was added and stirring was continued for a further 6 hours.

The mixture was added to diethyl ether/hexane (400 ml, 1:1) to precipitate the product. The product was collected by filtration, washed with diethyl ether and then dissolved from the filter with methanol. Removal of the methanol in vacuo gave a yellow powder.

This powder was stirred at room temperature in tetrahydrofuran (6 ml)/water (2 ml) with pyridinium p-toluenesulphonate (161 mg, 0.641 mmol). After 40 minutes, triethylamine (84 mg, 0.116 ml, 0.833 mmol) was added and the tetrahydrofuran was removed on the rotary evaporator. The aqueous residue was added to water (500 ml), and the precipitated product was collected by filtration and washed with water. The product was washed from the filter with tetrahydrofuran and the solvent was removed on the rotary evaporator. Purification by flash chromatography on silica gel (eluting with chloroform/methanol mixtures) gave the N-fluorenylmethoxycarbonyl derivative of the title compound (95 mg).

This product was stirred in dimethyl sulphoxide (3 ml)/methanol (0.5 ml) at room temperature and treated with piperidine (12.8 mg, 0.015 ml, 0.150 mmol). After 1.5 hours, the mixture was diluted with methanol (2 ml) and added to diethyl ether (400 ml). The precipitated product was collected by filtration, washed with diethyl ether and then dissolved from the filter with tetrahydrofuran/methanol. Removal of the solvent in vacuo and flash chromatography on silica gel (eluting with the lower phase of a 5:2:2 mixture of chloroform/methanol/0.880 ammonia solution) gave the title compound as a yellow solid. (E11)IR νmax (KBr disc): 3405 (broad), 2977, 2931, 1717, 1635, 1446, 1384, 1203, 1061, 1013, 972, 886, 852, 797cm$^{-1}$.

δH 400MHz (D$_4$-methanol/D$_5$ pyridine 1:1): 6.69–6.60 (2H,m), 6.56–6.27 (11H, series of m), 5.63 (1H,m), 5.50 (1H, dd, J 14.7, 10.2Hz), 4.81 (1H,s), 4.68–4.54 (3H,m), 4.46 (1H,m), 4.38 (1H,m), 4.22–4.12 (5H,m), 3.95 (1H,m), 3.84 (1H,m), 3.57 (1H,m), 3.49–3.40 (3H,m), 3.38 (1H,m), 3.30 (1H, ddd, J 13.5, 9.2, 4.1Hz), 2.85 (1H, dd, J 9.2, 3.0Hz), 2.62–2.48 (2H,m), 2.49 (1H, dd, A of ABX system, J 16.9, 9.6Hz), 2.35 (1H, dd, B of ABX system, J 16.8, 2.8Hz), 2.28 (1H, dd, J 12.0, 4.6Hz), 2.11 (1H,m), 2.06–1.42 (13H, series of m), 1.40 (3H, d, J 5.6Hz), 1.32–1.27 (9H,m), 1.24 (3H, d, J 6.4Hz), 1.17 (3H, d, J 7.1Hz).

Mass spectrum: FAB (Thiodiethanol/sodium) Observed mass 1068, calculated mass for C$_{51}$H$_{85}$N$_2$O$_{18}$PNa$^+$ 1067.6

EXAMPLE 12

16-Decarboxy-16-methylamphotericin B (E12)

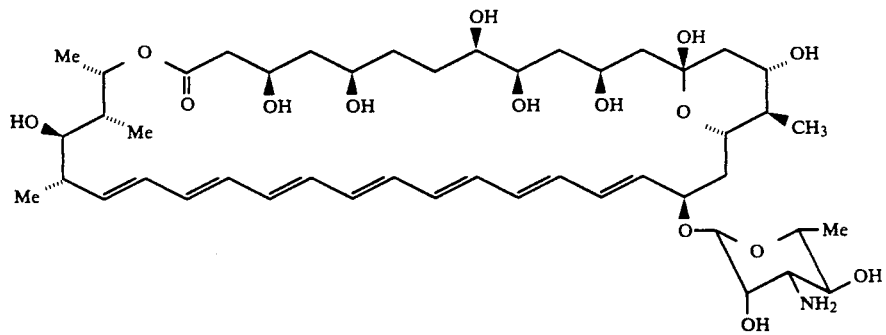

The title 16-methyl compound of Description 29 (95 mg, 0.084 mmol) and pyridinium p-toluenesulphonate (150 mg, 0.597 mmol) were stirred in tetrahydrofuran (4 ml)/water (2 ml) at room temperature. After 1.5 hrs, triethylamine (71 mg, 0.100 ml, 0.717 mmol) was added and the tetrahydrofuran was removed in vacuo. The aqueous residue was diluted with water (100 ml) and the precipitated product was collected by filtration, washed with water and dried to give a yellow powder. This product was dissolved in dimethyl sulphoxide (2.3 ml)/methanol (0.7 ml) and treated with piperidine (13 mg, 0.015 ml, 0.152 mmol). After 2.5 hrs, the mixture was diluted with methanol (1 ml) and added to diethyl ether (1 L). The precipitated product was collected by filtration, washed with diethyl ether and dried. Purification by flash chromatography on silica gel (eluting with the lower phase of a 3:1:1 mixture of chloroform:methanol:0.880 ammonia solution) gave the title compound (E12) as a yellow powder. IR νmax (KBr disc): 3420 (broad), 3013, 2967, 2928, 2880, 1717, 1626, 1456, 1384, 1320, 1269, 1178, 1069, 1012, 879, 852, 798cm$^{-1}$.

δH 400MHz (D$_4$-methanol/D$_5$-pyridine 1:1): 6.70–6.25 (13H, series of m), 5.61 (1H, dq, J 6.4 and 2.0Hz), 5.49 (1H, dd, J 14.6 and 10.1Hz), 4.80 (1H,s), 4.73–4.57 (2H,m), 4.44 (1H, tt, J 9.7 and 2.8Hz), 4.26 (1H,m), 4.13 (1H, d, J 2.8Hz), 4.00–3.81 (3H, series of m), 3.54–3.40 (3H, series of m), 3.36 (1H, dd, J 9.5 and 1.7Hz), 2.88 (1H,m), 2.56 (1H,m), 2.48 (1H, dd, J 16.8 and 9.7Hz, A of ABX system), 2.39 (1H,m), 2.34 (1H, dd, J 16.8 and 2.7Hz, B of ABX system), 2.24 (1H, dd, J 12.1 and 4.6Hz), 2.10 (1H,m), 2.05–1.92 (2H, series of m), 1.90–1.45 (11H, series of m), 1.43 (3H, d, J 5.7Hz), 1.34 (3H, d, J 6.4Hz), 1.23 (3H, d, J 6.4Hz), 1.16 (3H, d, J 7.1Hz), 1.15 (3H, d, J 6.4Hz) ppm.

Mass spectrum: FAB (Thiodiethanol/sodium matrix) observed mass 916 - calculated mass for C$_{47}$H$_{75}$O$_{15}$NNa$^+$, 916.5.

HPLC: Reverse phase ODS 5μ 250×4.6 mm column; eluent 82% methanol - 18% pH 3.5 phosphate buffer - 1 ml.min$^{-1}$; detection wavelength 350 nm; retention time: 8.2 minutes.

EXAMPLE 13

16-Decarboxy-16-methyl-13-O-methylamphotericin B
(E13)

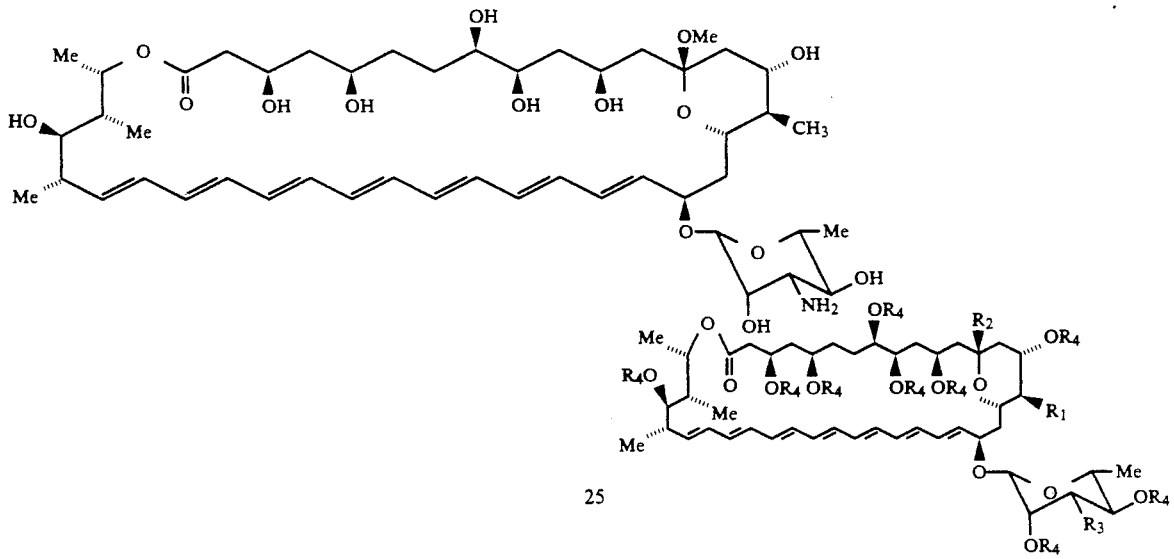

The title compound of Description 29 (45 mg, 0.040 mmol) and piperidine (7 mg, 0.008 ml, 0.082 mmol) were stirred at room temperature in dimethyl sulphoxide (1.2 ml)/methanol (0.3 ml). After 2.5 hrs, the mixture was diluted with methanol (0.5 ml) and added to diethyl ether (0.5L). The precipitated product was collected by filtration, washed with diethyl ether and dried. Purification by flash chromatography on silica gel (eluting with the lower phase of a 3:1:1 mixture of chloroform:methanol:0.880 ammonia solution) gave the title compound (E13) as a yellow powder.

IR $\nu$max (KBr disc): 3420 (broad), 3014, 2968, 2930, 2880, 1717, 1633, 1456, 1384, 1312, 1176, 1127, 1066, 1011, 986, 883, 852cm$^{-1}$, $\delta$H 400 MHz (D$_4$-methanol/D$_5$-pyridine 1:1): 6.60–6.25 (12H, series of m), 6.09 (1H, dd, J 14.8 and 7.7Hz), 5.58 (1H, dd, J 14.5 and 9.7Hz), 5.53 (1H, m), 4.79 (1H,s), 4.72 (1H, m), 4.47 (1H, tt, J 9.3 and 3.2Hz), 4.18 (1H,m), 4.13 (1H, d, J 3.0Hz), 3.98 (1H,m), 3.86–3.70 (3H, series of m), 3.55–3.40 (4H, series of m), 3.25 (3H,s), 2.82 (1H, dd, J 9.2 and 3.0Hz), 2.56 (1H,m), 2.52 (1H, dd, J 16.2 and 9.1Hz, A of ABX system), 2.40 (1H, dd, J 16.5 and 3.3Hz, B of ABX system), 2.36 (1H,m), 2.21 (1H,m), 2.13–1.91 (5H, series of m), 1.85–1.50 (9H, series of m), 1.44 (3H, d, J 5.7Hz), 1.35 (3H, d, J 6.4Hz), 1.24 (3H, d, J 6.5Hz), 1.17 (3H, d, J 6.3Hz), 1.15 (3H, d, J 7.1Hz) ppm.

Mass spectrum: FAB (Thiodiethanol/sodium matrix) observed mass 930 - calculated mass for C$_{48}$H$_{77}$O$_{15}$. NNa$^+$, 930.5.

HPLC: Reverse phase ODS 5$\mu$ 250×4.6mm column; eluent 82% methanol - 18% pH 3.5 phosphate buffer - 1 ml.min$^{-1}$; detection wavelength 350 nm; retention time: 5.8 minutes.

We claim:

1. A compound of formula (I) or a pharmaceutically acceptable salt thereof:

(I)

wherein R$_1$ is selected from the group consisting of a group —CH$_2$—X where X is hydrogen, halogen, —CN, —N$_3$, —OC(O)R$_5$, —S(O)$_n$R$_5$, —SH, —OC(O)NHR$_5$, —NHCONHR$_5$ or —NR$_6$R$_7$, where R$_5$ is hydrogen, C$_{1-8}$ alkyl, phenyl, naphthyl, heteroaryl, aryl-C$_{1-4}$ alkyl or heteroaryl-C$_{1-4}$ alkyl in each of which the aromatic moiety is optionally substituted with the proviso that when X is —S(O)$_n$R$_5$, R$_5$ does not represent hydrogen, R$_6$ and R$_7$ are independently hydrogen or C$_{1-8}$ alkyl, or one of R$_6$ and R$_7$ is hydrogen and the other is -formyl, C$_{2-8}$ alkanoyl, dialkoxyphosphoryl, aroyl, heteroaroyl, aryl-C$_{1-4}$ alkanoyl, heteroaryl-C$_{1-4}$ alkanoyl, C$_{1-8}$ alkylsulphonyl, arylsulphonyl, heteroarylsulphonyl, aryl-C$_{1-4}$ alkylsulphonyl or heteroaryl-C$_{1-4}$ alkylsulphonyl, where n is 0, 1 or 2 and any R$_5$ C$_{1-8}$ alkyl and R$_5$, R$_6$ or R$_7$ aryl or heteroaryl moieties are optionally mono-, di-, or tri-substituted by any function selected from the group consisting of carboxy, nitro, alkoxycarbonyl, OH, C$_{1-6}$ alkyl, C$_{1-6}$ alkoxy, halogen and NR$_6$R$_7$; R$_2$ is hydroxy or C$_{1-8}$ alkoxy; R$_3$ is an amino group or an acyl derivatives thereof, selected from the group consisting of N-D-lysyl, N-D-ornithyl, guanidine and N-glycosyl; and each R$_4$ is hydrogen.

2. A compound according to claim 1, wherein R$_2$ is hydroxy or methoxy.

3. A compound according to claim 1, wherein R$_1$ is selected from the group consisting of —CH$_2$N$_3$, —CH$_2$NH$_2$, —CH$_2$S-phenyl, CH$_2$I, —CH$_2$CN, —CH$_2$OC(O)CH$_3$, —CH$_2$NHCOCH$_3$, —S(O)$_n$R$_5$ where R$_5$ is 4-methylphenyl and n is 2, —CH$_2$NHP(O)(OEt)$_2$ and CH$_3$.

4. A compound according to claim 1, wherein R$_3$ is amino.

5. A compound selected from the group consisting of:
16-azidomethyl-16-decarboxyamphotericin B,
16-azidomethyl-16-decarboxy-13-O-methylamphotericin B,
16-aminomethyl-16-decarboxy-13-O-methylamphotericin B,
16-decarboxy-16-phenylthiomethylamphotericin B, 16-decarboxy-16-iodomethylamphotericin B,
16-cyanomethyl-16-decarboxy-13-O-methylamphotericin B,
16-cyanomethyl-16-decarboxyamphotericin B,
16-acetoxymethyl-16-decarboxyamphotericin B,
16-acetamidomethyl-16-decarboxyamphotericin B,
16-decarboxy-16-(p-toluenesulphonamidomethyl)amphotericin B,
16-decarboxy-16-(diethoxyphosphoramido)methylamphotericin B,
16-decarboxy-16-methylamphotericin B and
16-decarboxy-16-methyl-13-O-methylamphotericin B.

6. A pharmaceutical composition comprising a compound of formula (I), as defined in claim 1, or a pharmaceutically acceptable salt thereof together with a pharmaceutically acceptable diluent or carrier.

7. A method of treatment of fungal infections caused by Candida, Trichophyton, Microsporum, Epidermophyton, Cryptococcus, Aspergillus, Coccidiodes, Paracoccidiodes, Histoplasma and Balstomyces in animals, including humans, which comprises administering an effective antifungal amount of a compound of formula (I) as defined in claim 1 or a pharmaceutically acceptable salt thereof to the animal in need of such treatment.

* * * * *